United States Patent [19]
Kraus et al.

[11] Patent Number: 5,209,728
[45] Date of Patent: May 11, 1993

[54] LOW PROFILE, HIGH PERFORMANCE INTERVENTIONAL CATHETERS

[75] Inventors: Jeff Kraus, San Jose; Robert D. Lashinski, Cupertino, both of Calif.

[73] Assignee: Danforth Biomedical, Inc., Menlo Park, Calif.

[21] Appl. No.: 946,828

[22] Filed: Sep. 16, 1992

Related U.S. Application Data

[63] Continuation of Ser. No. 430,702, Nov. 2, 1989, abandoned.

[51] Int. Cl.⁵ ............................................ A61M 29/00
[52] U.S. Cl. ...................................... 604/96; 604/280
[58] Field of Search ................... 604/95, 96, 100–104, 604/280–283; 606/170, 194; 128/325, 344, 348.1

[56] References Cited

U.S. PATENT DOCUMENTS

| | | |
|---|---|---|
| Re. 33,166 | 2/1990 | Samson . |
| 4,195,637 | 4/1980 | Gruntzig et al. . |
| 4,299,226 | 11/1981 | Banka . |
| 4,448,195 | 5/1984 | LeVeen et al. . |
| 4,473,067 | 9/1984 | Schiff . |
| 4,573,470 | 4/1986 | Samson et al. . |
| 4,582,181 | 5/1986 | Samson . |
| 4,616,653 | 10/1986 | Samson et al. . |
| 4,638,805 | 1/1987 | Powell . |
| 4,641,654 | 2/1987 | Samson et al. . |
| 4,664,113 | 5/1987 | Frisbie et al. . |
| 4,715,378 | 12/1987 | Pope, Jr. et al. . |
| 4,726,374 | 2/1988 | Bales . |
| 4,748,982 | 6/1988 | Horzewski et al. . |
| 4,762,129 | 8/1988 | Bonzel . |
| 4,790,315 | 12/1988 | Mueller, Jr. et al. . |
| 4,793,350 | 12/1988 | Mar et al. . |
| 4,808,164 | 2/1989 | Hess . |
| 4,811,737 | 5/1989 | Rydell . |
| 4,813,934 | 3/1989 | Engelson et al. . |
| 4,821,722 | 4/1989 | Miller et al. . |
| 4,838,268 | 6/1989 | Keith et al. . |
| 4,846,174 | 7/1989 | Willard et al. . |
| 4,875,481 | 10/1989 | Higgins . |
| 4,892,519 | 1/1990 | Songer et al. . |
| 4,896,670 | 1/1990 | Crittenden . |
| 4,906,241 | 3/1990 | Noddin et al. . |
| 4,917,088 | 4/1990 | Crittenden . |
| 4,927,413 | 5/1990 | Hess . |
| 4,943,278 | 7/1990 | Euteneuer et al. . |
| 4,955,384 | 9/1990 | Taylor et al. . |
| 4,990,139 | 2/1991 | Jang . |

FOREIGN PATENT DOCUMENTS

| | | |
|---|---|---|
| 0279959 | 8/1988 | European Pat. Off. . |
| 0397038 | 5/1990 | European Pat. Off. . |
| 0398676 | 5/1990 | European Pat. Off. . |
| 0374859 | 6/1990 | European Pat. Off. . |
| 0376132 | 7/1990 | European Pat. Off. . |
| 8606285 | 11/1986 | PCT Int'l Appl. . |
| 9007909 | 7/1990 | PCT Int'l Appl. . |

OTHER PUBLICATIONS

Datascope Integra PTCA Dilatation Catheter (author and date unknown).
1989 Datascope Annual Report—three pages (author and date unknown).

*Primary Examiner*—John D. Yasko
*Attorney, Agent, or Firm*—Townsend and Townsend Khourie and Crew

[57] ABSTRACT

A catheter, having a substantially fluid-tight seal is provided. The seal can be used in a number of catheters, including an angioplasty catheter. The seal includes surfaces that are independently movable relative to one another. The effectiveness of the seal depends on the proximity of the surfaces, the surface are at the interface, pressure differential and viscosity of the fluid. The seal is used in connection with providing fluid-tight channels with surfaces that are relatively movable and to circumvent the need to separate hydraulic channels from other channels so that catheters can be provided with fewer channels. Further, catheters and catheter systems with smaller shaft dimensions or larger hydraulic channel dimensions is made possible. Balloon catheters using this seal have enhanced torque delivery and directional control.

16 Claims, 12 Drawing Sheets

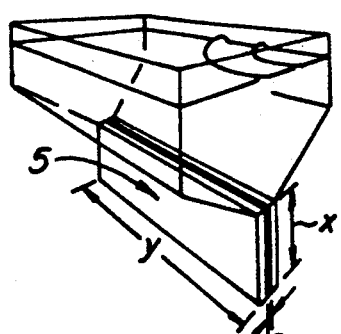
FIG._1A.
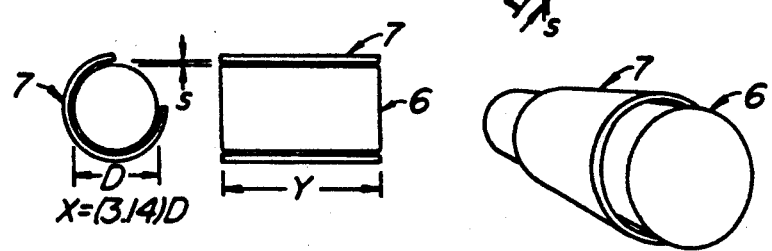
FIG._1B.
$X = (3.14)D$
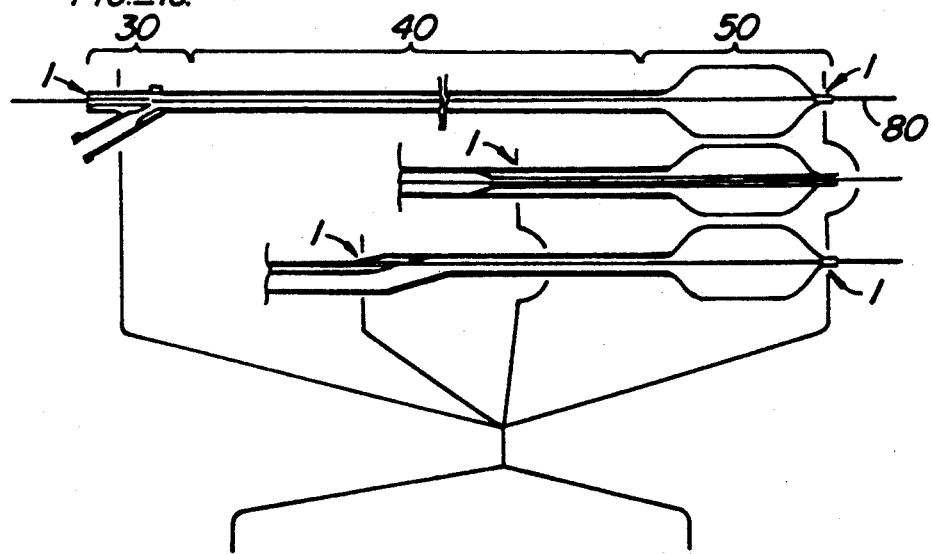
FIG._1C.
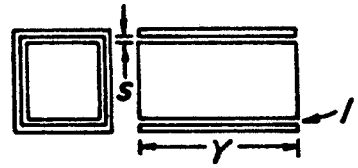
FIG._1D.
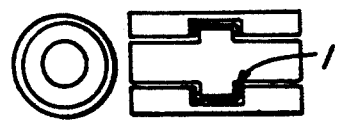
FIG._1E.
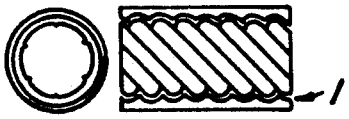
FIG._1F.
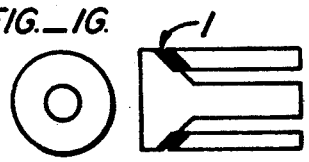
FIG._1G.
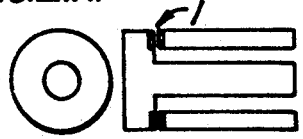
FIG._1H.

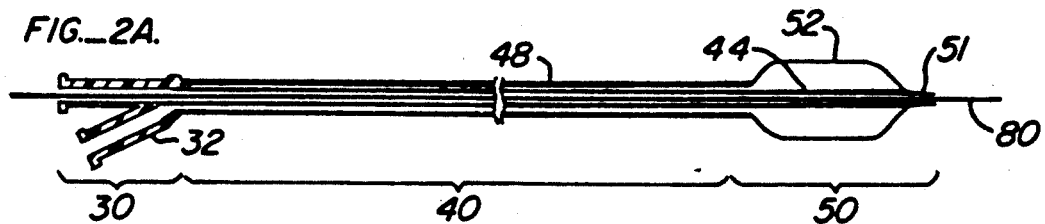
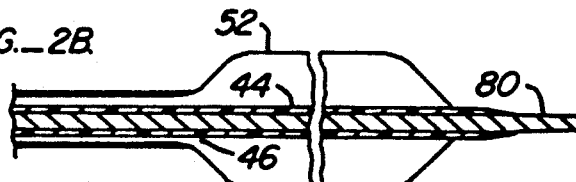
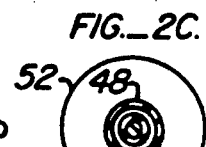
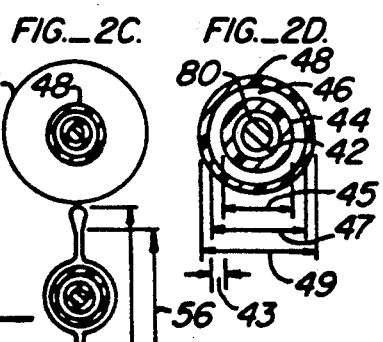
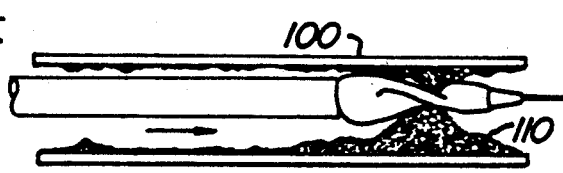
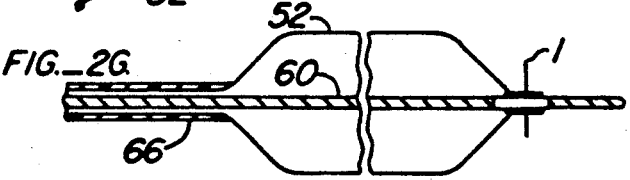
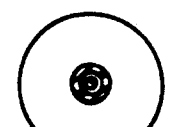
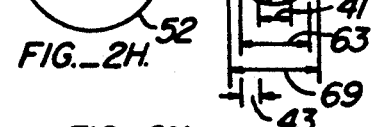
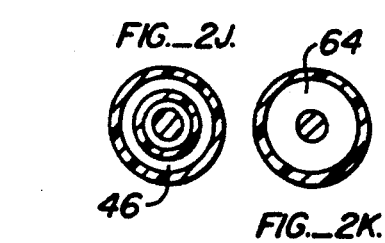

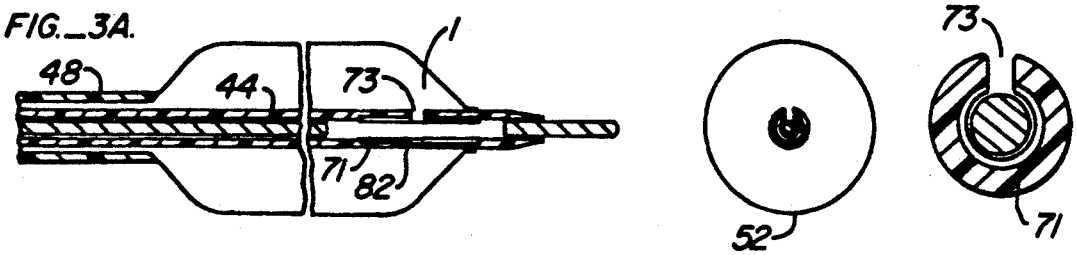
FIG._3A.
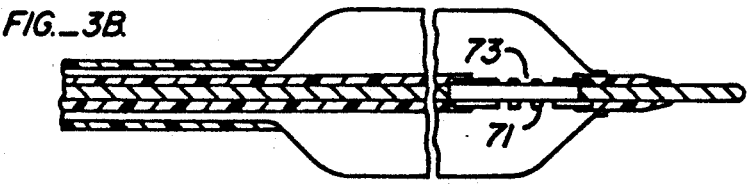
FIG._3B.
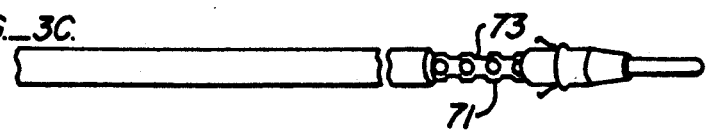
FIG._3C.
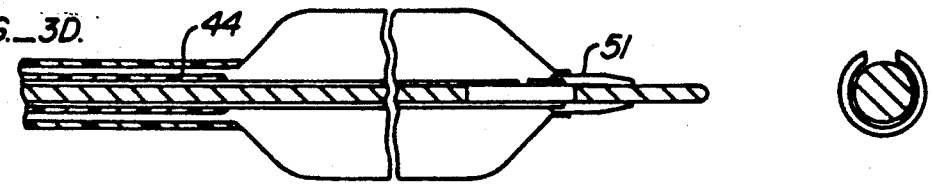
FIG._3D.
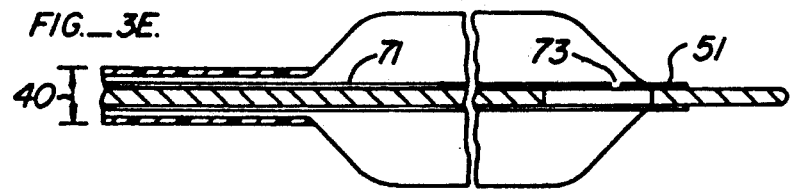
FIG._3E.
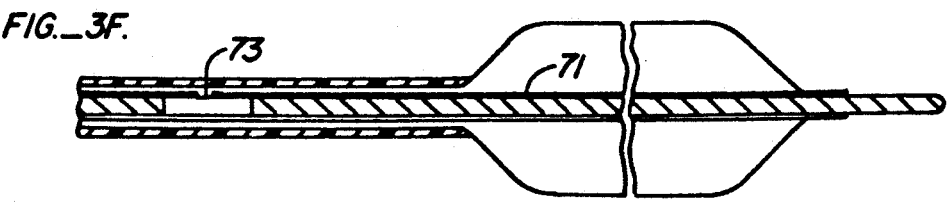
FIG._3F.

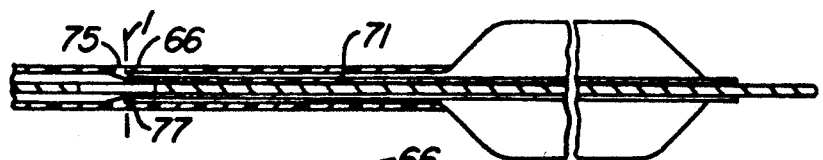
FIG._4A.
FIG._4B.
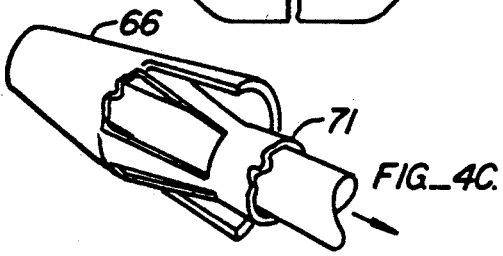
FIG._4C.
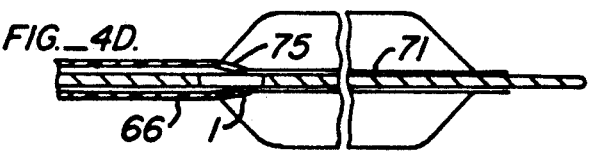
FIG._4D.
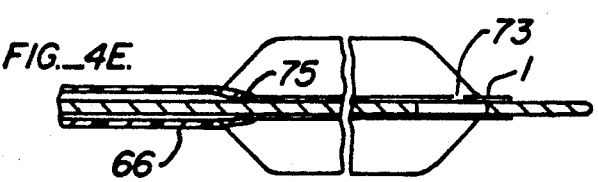
FIG._4E.
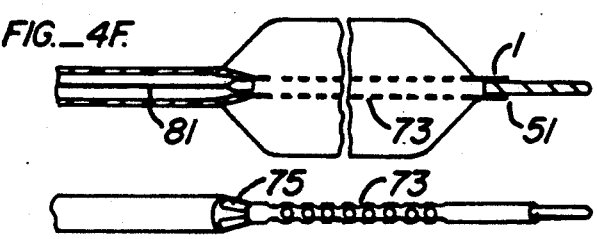
FIG._4F.
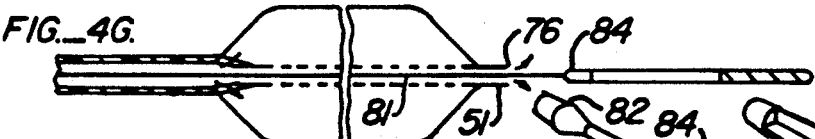
FIG._4G.
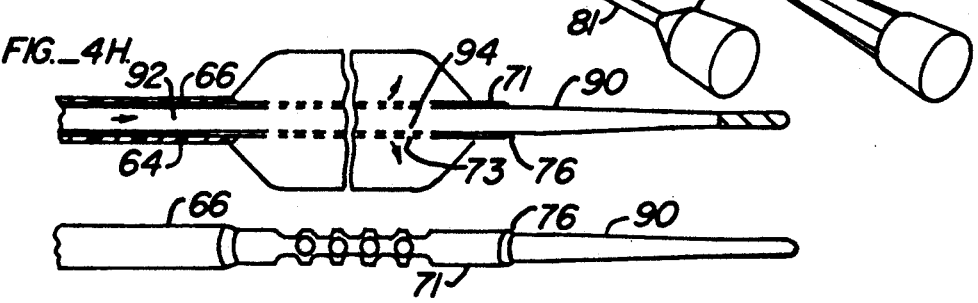
FIG._4H.
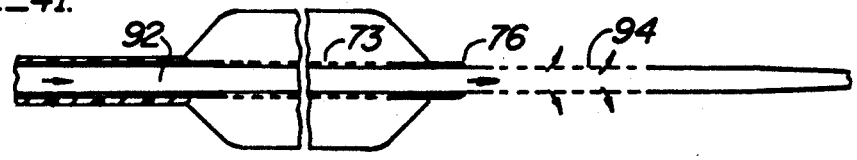
FIG._4I.

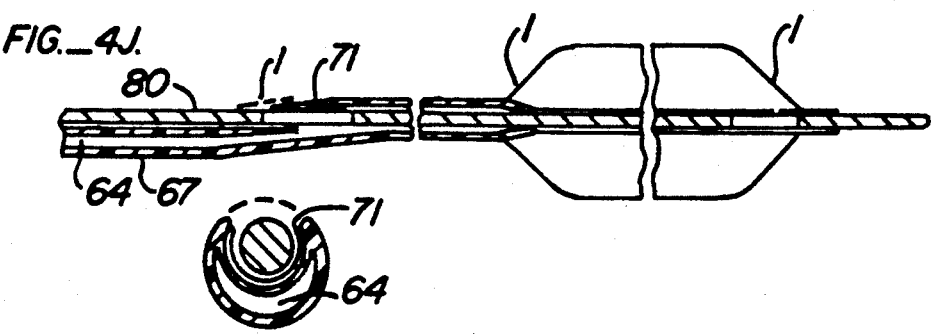
FIG._4J.
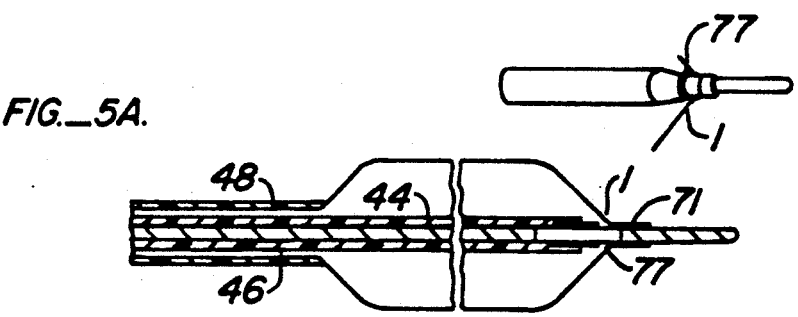
FIG._5A.
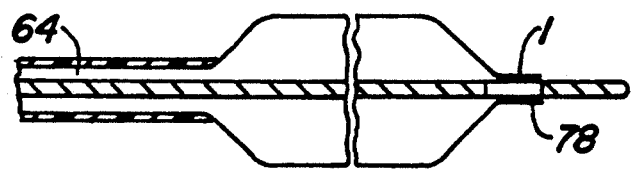
FIG._5B.
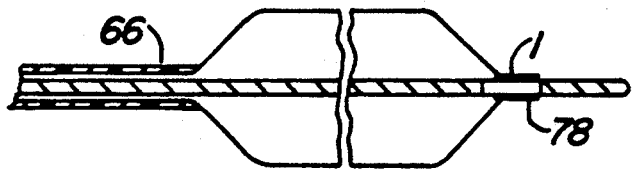
FIG._5C.
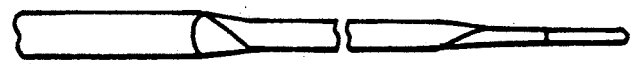
FIG._5D.
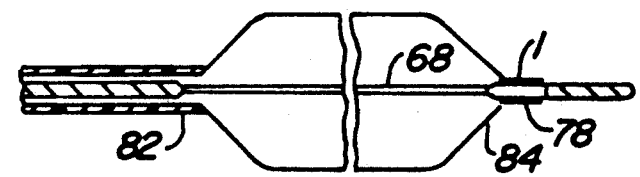
FIG._5E.
FIG._5F.

FIG._6A.
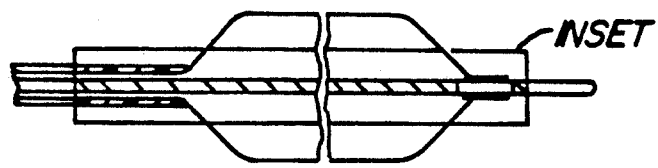
FIG._6B.
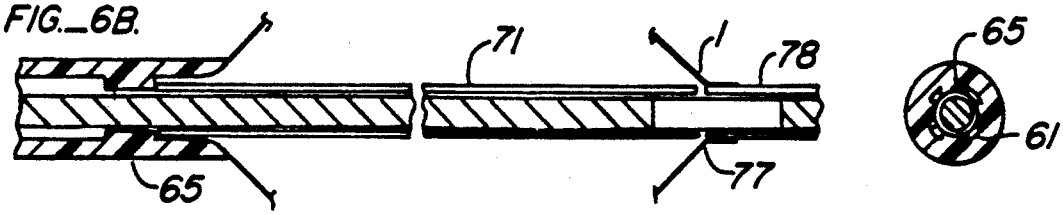
FIG._6C.
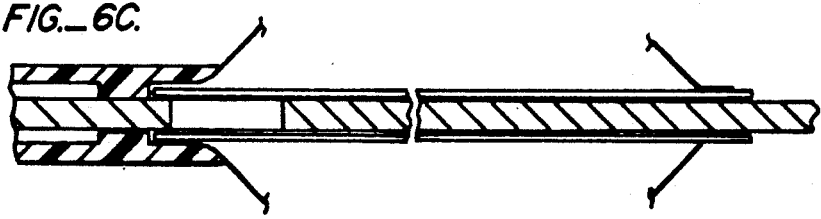
FIG._6D.
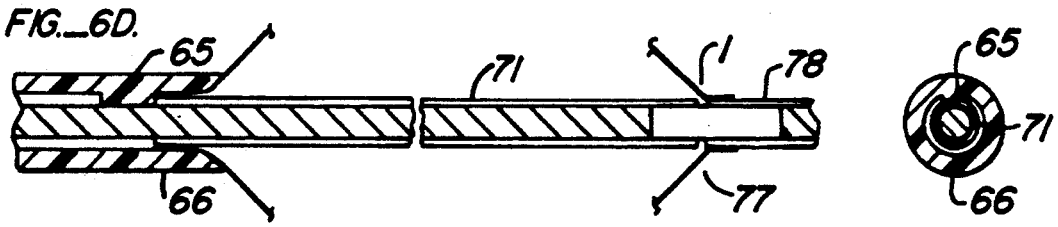
FIG._6E.
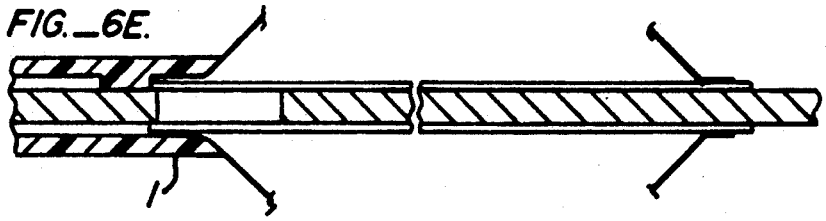

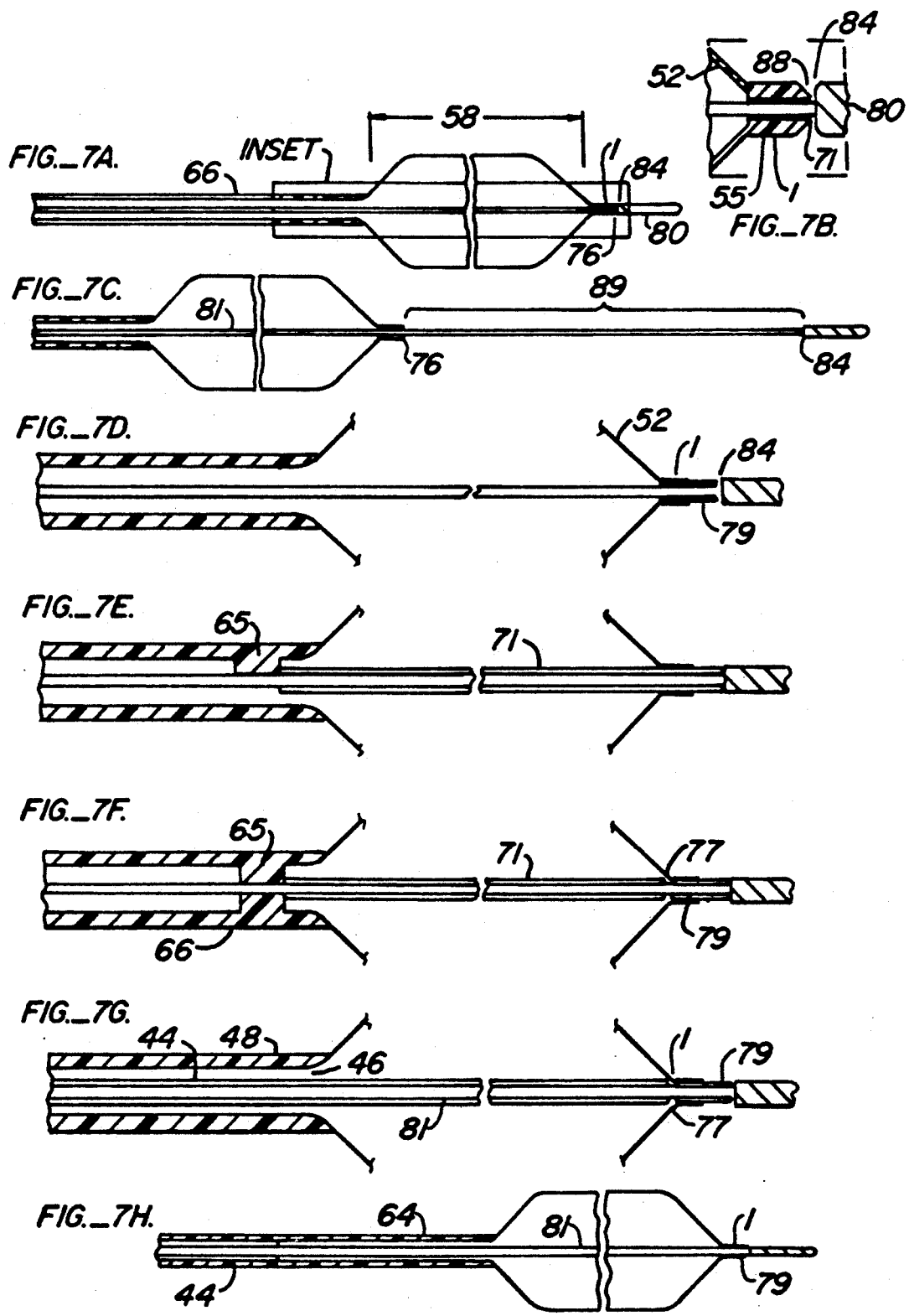

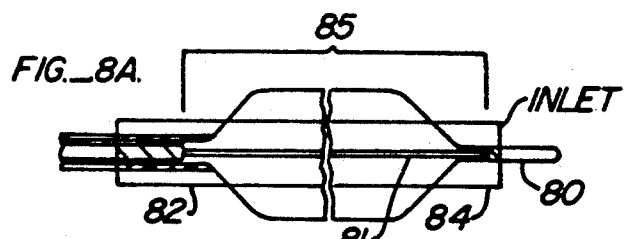
FIG._8A.
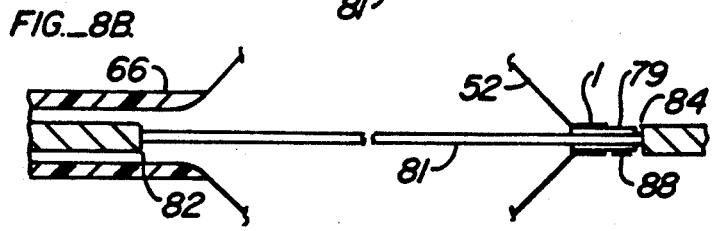
FIG._8B.
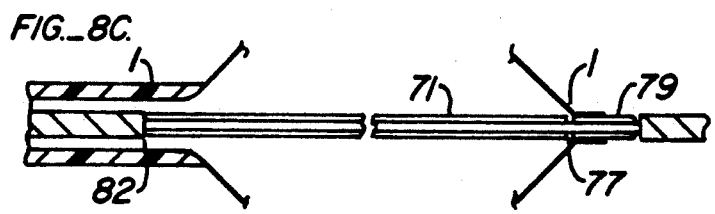
FIG._8C.
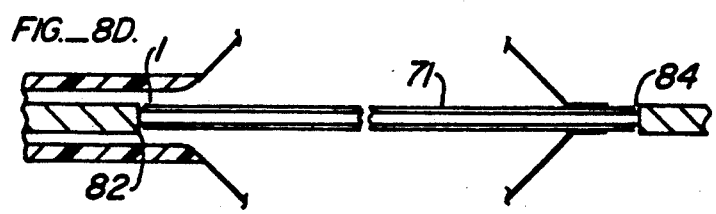
FIG._8D.
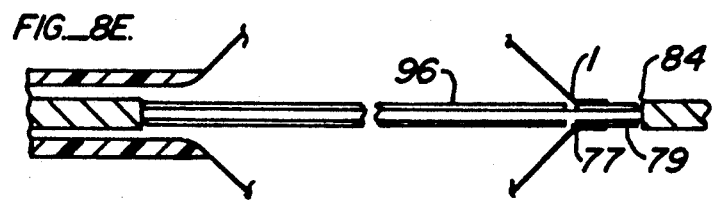
FIG._8E.
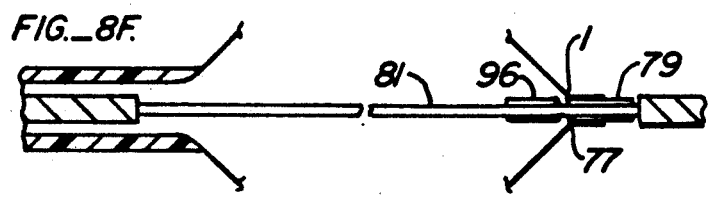
FIG._8F.
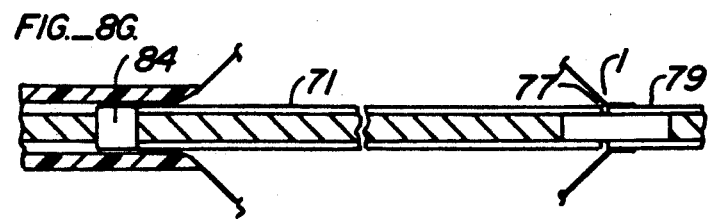
FIG._8G.
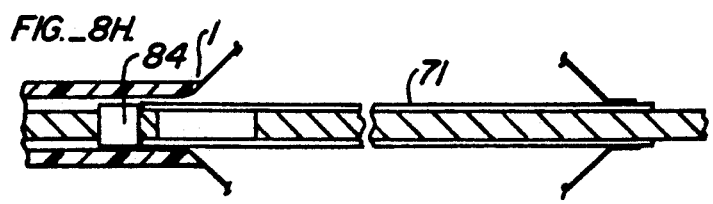
FIG._8H.

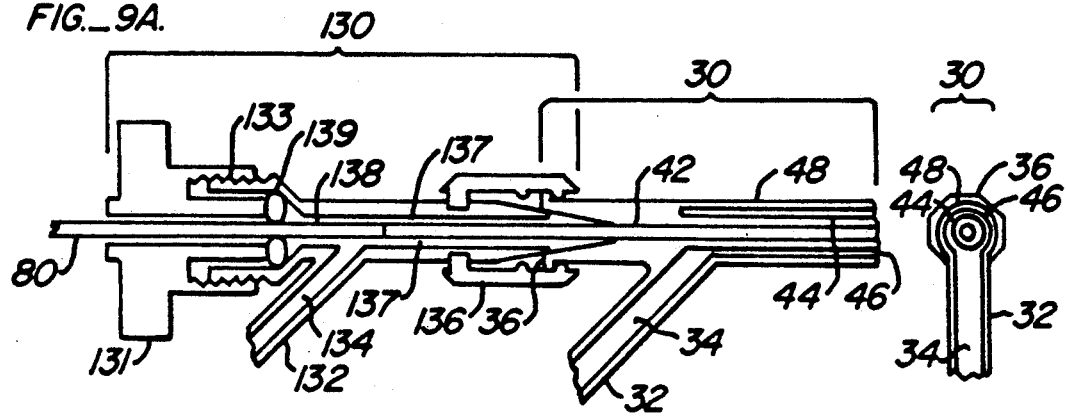
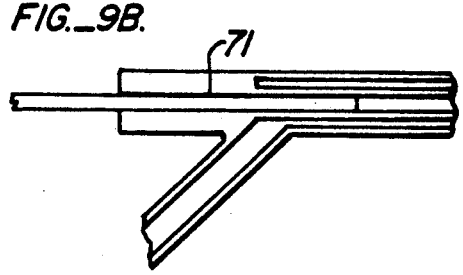
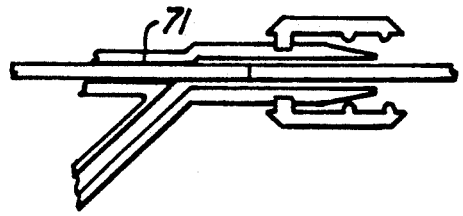
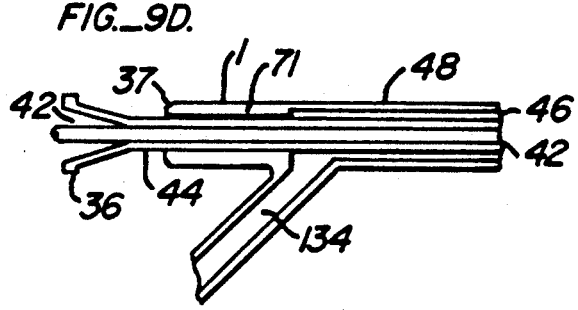
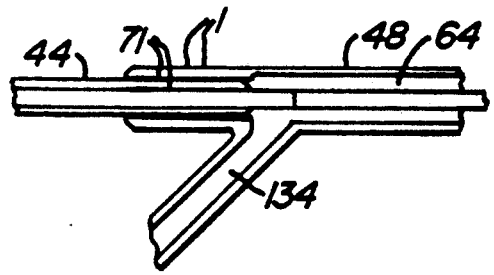
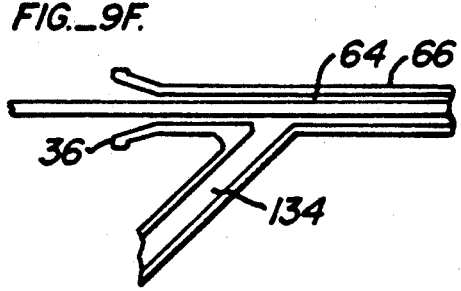
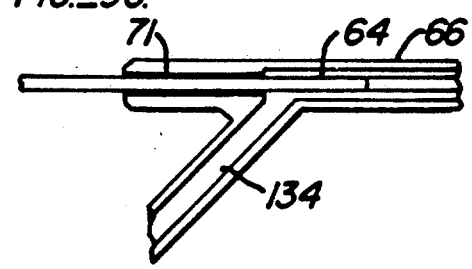

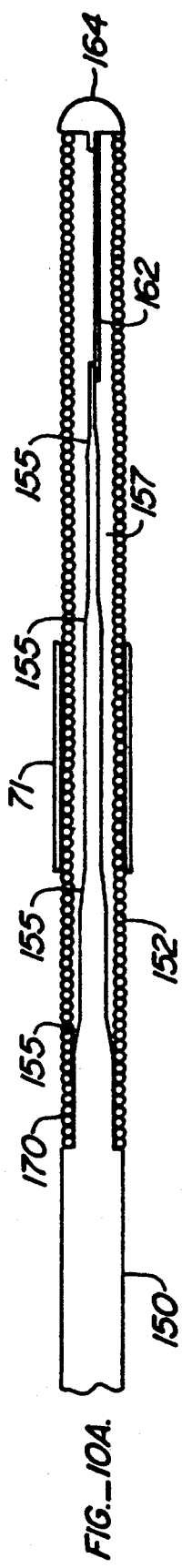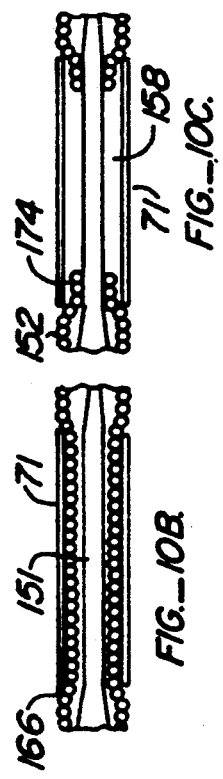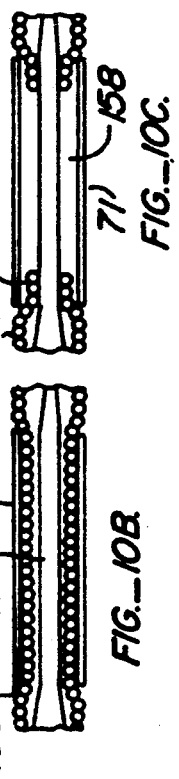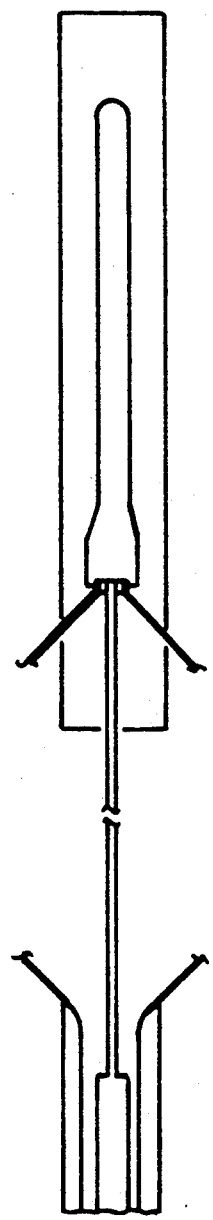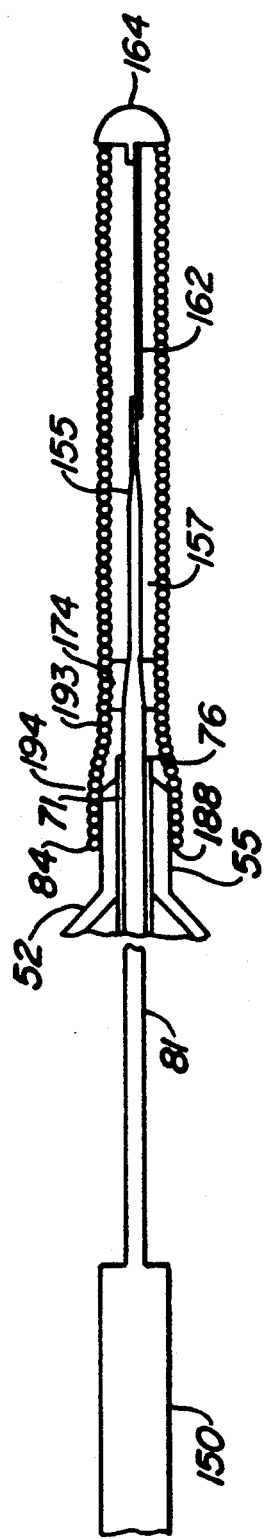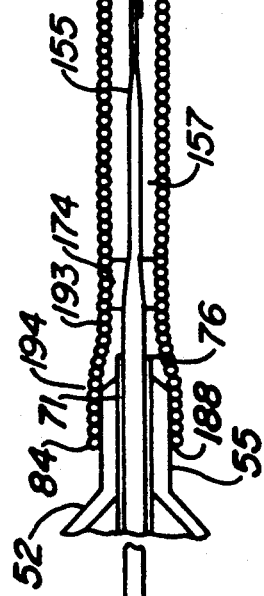

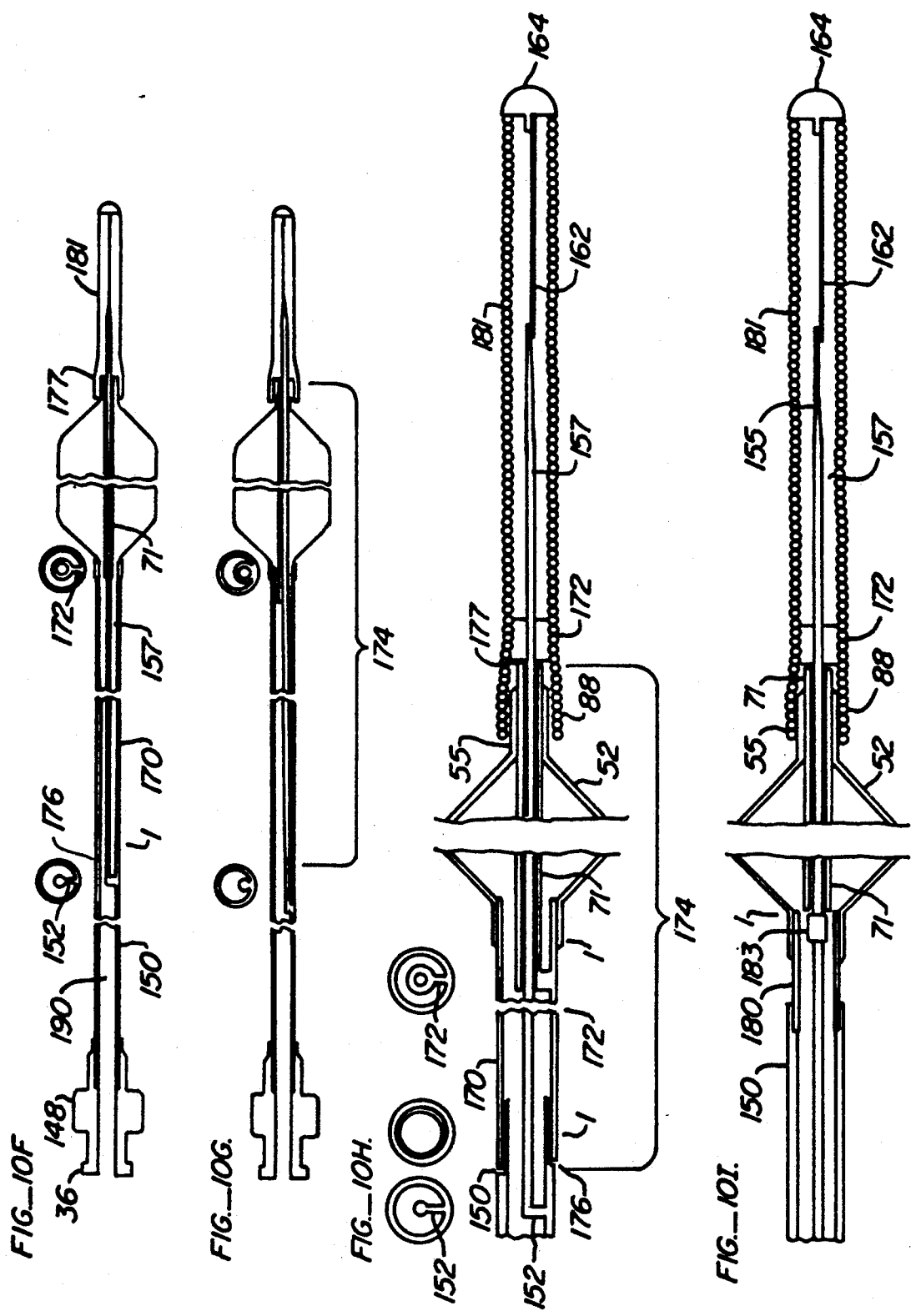

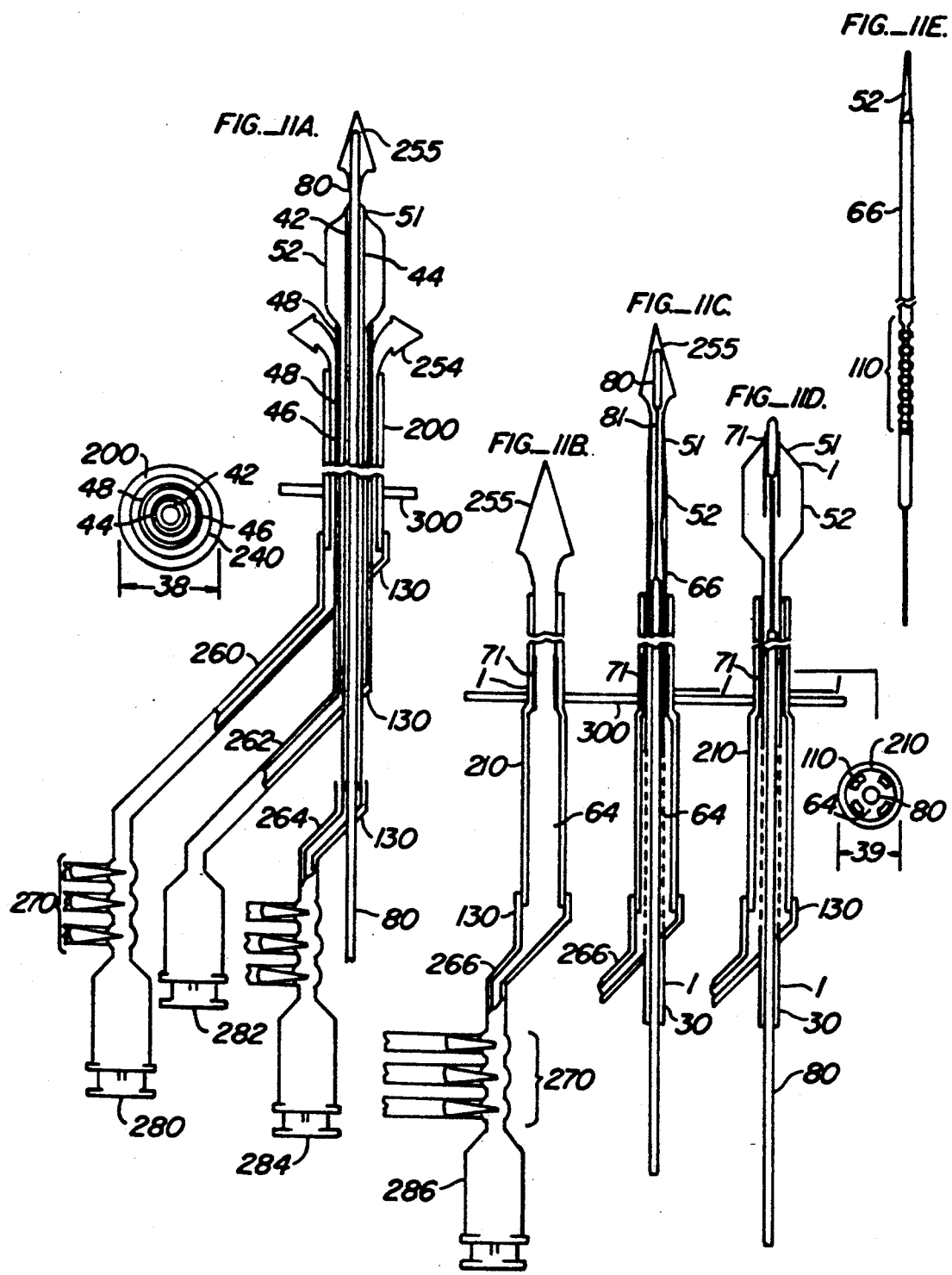

LOW PROFILE, HIGH PERFORMANCE INTERVENTIONAL CATHETERS

This is a continuation of application Ser. No. 07/430,702 filed Nov. 2, 1989, now abandoned.

BACKGROUND OF THE INVENTION

1. Field of the Invention

This invention relates to catheters and catheter systems. In particular this invention relates to seals in catheters, particularly to angioplasty catheters.

2. Background Description

At present, there exist four distinct functional classes of dilatation balloon catheters/catheter systems: (1) "over-the-wire" catheter systems, (2) "semi-movable" catheter systems, (3) "fixed-wire" catheter systems, and (4) "balloon-on-a-wire" devices. "Over-the-wire" catheter systems permit full rotational and full coaxial mobility of the guidewire relative to the catheter component of the system. "Over-the-wire" catheter systems are the only dilatation balloon angioplasty systems of the prior art that permit separation of the catheter component from the guidewire component. "Over-the-wire" catheters can be fully withdrawn over a guidewire, and they will accept the antegrade and retrograde introduction of a guidewire therethrough. U.S. Pat. No. 4,323,071 describes an "over-the-wire" system. "Semi-movable" catheter systems permit full rotational and limited coaxial mobility of the guidewire installed therein. U.S. Pat. No. 4,616,653 describes a "semi-movable" system. "Fixed-wire" catheter systems permit limited rotation mobility and no coaxial mobility of the guidewire relative to the catheter component of the system. U.S. Pat. No. 4,582,181 describes a "fixed-wire" system. "Balloon-on-a-wire" devices do not provide any mobility of the guidewire relative to the balloon component of the system. Rotation of the directional guidewire disposed at the distal aspect of these devices requires rotation of the entire device. International Patent Application No. PCT/US86/00938 entitled "Microdilatation Probe and System for Performing Angioplasty" describes a "balloon-on-a-wire" device.

"Over-the-wire" systems were the first systems introduced that provided satisfactory "steerability." FIGS. 2A–2E have been included in this application to illustrate the design features fundamental to "over-the-wire" systems currently marketed worldwide. Importantly, note that the shaft of the catheter 40 contains two separate lumens 42,46 which function independently to accommodate a guidewire 80 and to transmit fluid and hydraulic pressure along the length of the catheter. Occasionally, these catheters are constructed with three shaft lumens with the third functioning as a vent for the balloon. The proximal end 30 of the catheter contains an adapter 32 designed to interface with a source of hydraulic pressure, while the distal end 50 contains a "balloon-like" structure 52 for dilation of the artery or other vessel. In the case of the catheter illustrated in FIGS. 2A–2E, the catheter is composed of two pieces of concentric tubing. Although alternative designs exist for the construction of multi-lumen dilatation balloon catheters, it should be recognized that the fundamental features of all prior art "over-the-wire" catheters are similar. For the purpose of simplicity, we will confine our remarks concerning "over-the-wire" catheters to the catheter configuration depicted in FIGS. 2A–2E, with the understanding that these remarks apply to all prior art "over-the-wire" devices, regardless of configuration.

The design features that distinguish "semi-movable" systems from "over-the-wire" systems concern: (1) the profile of the segment of the guidewire contained within the catheter component of the device and (2) the permanence of the guidewire within the confines of the catheter. The guidewires contained within these devices are significantly lower in profile relative to the profiles of stand alone guidewires used in conjunction with "over-the-wire" systems. In fact, the guidewires contained within these devices have been rendered sufficiently low in profile and thus sufficiently delicate that they cannot tolerate the abuse that stand-alone guidewires commonly receive during the course of a routine angioplasty procedure. As a result, "semi-movable" devices have been designed such that the guidewires cannot be removed from the protective confines of the catheter shaft.

A "fixed" guidewire/catheter composite system consists of a single-lumen dilatation balloon catheter that contains a low profile guidewire which extends therethrough. The catheter and guidewire are immovably bonded together at the distal aspect of the balloon component of the catheter. These devices are commonly manufactured with a "torque limiter" that functions to limit the rotational mobility of the guidewire relative to the catheter component of these systems. The guidewire provides column strength for the balloon.

A "balloon-on-a-wire" system, as the name implies, consists of a guidewire that contains a lumen which communicates with a balloon disposed on the shaft of the guidewire. The balloon is immovably bonded to the guidewire.

The balloon component 52 of a conventional dilatation catheter usually is referred to as a "balloon-like" structure because the balloon component is not a true balloon. The "balloon-like" segment consists of an aneurism within a segment of the tubing 48, that has a lumen that extends therethrough. In the case of "over-the-wire" and "semi-movable" systems, the hydraulic competence of the "balloon component" is achieved by bonding the inner surface of tubing 48 to the outer surface of a length of tubing 44 contained therein at the distal aspect of the device 51. In the case of "fixed-wire" and "balloon-on-a-wire" systems, hydraulic competence is achieved by bonding the balloon component onto the guidewire that extends therethrough.

Considerable effort has been directed toward the development of dilatation balloon catheters with progressively smaller cross-sectional profiles. Catheters with lower profiles provide several advantages. They provoke less trauma during the process of introduction within the intra-vascular system. They require less effort to manipulate across severe obstructions, and they create less impairment to blood flow within the vessel containing the device (as illustrated in FIG. 2E).

A small profile also permits superior intraoperative angiographic delineation of the vascular system relative to larger profile catheters. Angiograms must be obtained intermittently during the course of a routine angioplasty procedure to reassess the vascular anatomy. This is generally accomplished by injecting contrast media into the vascular system via the guiding catheter that contains the dilatation balloon catheter. (Contrast media is a radio-opaque liquid that functions to opacify the vasculature when injected during the performance of an arteriogram.) The resolution of conventional angiography is directly related to the rate of contrast injection, which, in turn, is directly related to the cross-sectional area of the channel used to convey the contrast media into the intra-vascular system. During the course of an angioplasty, the cross-sectional area of this channel effectively equals the cross-sectional area of the lumen of the guiding catheter minus the corresponding cross-sectional area of the shaft of the dilatation catheter contained therein. The use of dilatation catheters with lower shaft profiles thus permits the delivery of higher flow rates of contrast fluid to permit the performance of intra-operative angiography with enhanced resolution.

In short, lower profile catheters are easier and safer to use relative to larger profile counterparts. Their use provokes less trauma, both during introduction into the vascular system and during manipulation across an intra-vascular stenosis. Low profile devices further provoke less impairment of blood flow and permit superior angiographic definition of the vascular anatomy relative to larger profile devices. Hence, considerable effort has been devoted to their development.

Although considerable progress has evolved in this regard, it should be recognized that much of the progress concerning "over-the-wire" systems has resulted from the process of miniaturization. The use of state-of-the-art plastics has permitted the manufacture of these devices with progressively thinner walls. The development of new technologies has permitted the construction of these devices with progressively smaller caliber channels. Relatively little benefit has resulted from efforts to modify the fundamental "over-the-wire" catheter design, which has remained essentially unchanged since it was introduced.

Despite the progress that has been achieved as a result of miniaturization, this practice has provided gradually diminishing returns. In addition, it has been responsible for the development of several functional limitations. This process accounts for the fact that current generation low profile "over-the-wire" catheter systems have (1) compromised "pushability," (2) compromised balloon inflation/deflation rates, (3) limited guidewire compatibility, (4) compromised guidewire torque transmission, (5) compromised trackability, (6) enhanced propensity for air entrapment, (7) enhanced balloon fragility, and (8) lowered balloon profiles, relative to larger profile devices.

With respect to the first issue, the "pushability," or column strength, of a catheter varies directly with the rigidity of the plastic that is used in the construction of the shaft as well as the thickness of the walls used in the construction of the catheter shaft. Conventional low profile systems tend to have inferior "pushability" relative to larger profile systems because the channel walls of these devices tend to be thinner. As a result, low profile devices are prone to axial compression and buckling during introduction within critical stenoses, two features that limit their utility in the treatment of high grade lesions. This circumstance has been partially offset by the use of more rigid plastics in the construction of these devices.

With respect to the second issue, prolonged inflation/deflation times, the rate of inflation and deflation of the "balloon-like" component of a dilatation balloon catheter is directly related to the cross-sectional area of the hydraulic channel 46 that communicates with the balloon and conveys the hydraulic pressure along the length of the catheter, and to the viscosity of the hydraulic medium that is used to transmit the hydraulic pressure. Because the channels contained within low profile systems of the prior art tend to be smaller relative to prior generation catheters, the corresponding inflation and deflation times for these devices tend to be longer. This feature enhances the risk of provoking ischemically-mediated complications with the use of these devices. This circumstance derives from the fact that partial balloon inflation compromises blood flow and accomplishes no therapeutic benefit. Balloons are partially inflated during the process of balloon inflation and deflation. Again, this adverse feature has been partially offset by the use of more rigid plastics in the construction of the catheter shaft. This practice has permitted the manufacture of the shafts with thinner walls and hence larger lumens relative to previous generation devices.

With respect to the third issue of guidewire compatibility, the larger guidewires (e.g., 0.018 inch diameter) are preferred by most operators for procedures involving critical stenoses, the very lesions for which the low profile catheters were developed. This preference arises because the larger profile guidewires offer greater stability, offer greater structural integrity, transmit greater torque, tolerate greater force, and permit superior steerability relative to smaller profile guidewires. In short, these wires can be negotiated within the confines of complex or high grade lesions more reliably and more consistently relative to lower profile wires. Because the guidewire channels of low profile systems tend to be small, they frequently cannot accommodate the large profile wires. Hence, the use of low profile catheters frequently obligates the concomitant use of low profile guidewires, a requirement that predisposes the patient receiving the procedure to enhanced morbidity relative to the optimal circumstance.

With respect to the fourth issue, compromised guidewire torque transmission, the efficiency with which torque is transmitted via the guidewire is inversely related to the friction generated by rotation of the guidewire within the confines of the guidewire catheter channel. Torque transmission is required to direct the guidewire within the patient's vasculature. Clearly, the amount of friction that develops in response to guidewire rotation is a function of the extent to which the outside surface of the guidewire contacts the luminal surface of the guidewire channel and to the coefficient of friction of the guidewire, catheter interface. And the propensity for guidewires to come in contact with the luminal surface of catheters increases as the profile of the guidewire channel is reduced. Because low profile catheters contain smaller guidewire channels, they provide diminished guidewire torque delivery and hence diminished directional control, relative to larger profile devices. This circumstance has been partially offset by the application of a lubricous coating to the guidewires contained within these systems.

With respect to the fifth issue, compromised catheter "trackability," the ease with which a catheter courses over a guidewire varies as a function of: (1) the resistance generated between the catheter and guidewire during coaxial movement of the catheter relative to the guidewire, and (2) the flexibility of the catheter component of the system. Hence, the "trackability" of a catheter relates in part to the size of the guidewire channel. Because lower profile catheters contain lower profile guidewire channels relative to the larger profile devices, these devices provide less "trackability" relative to the larger profile devices. This circumstance has been partially offset by: the manufacture of these devices with thinner walls and hence more flexible catheter shafts, and the use of lubricous coatings on the surfaces common to the guidewire and guidewire catheter channels of these devices.

With respect to the sixth issue, air entrapment, the air must be evacuated from the hydraulic channel of all dilatation balloon catheters before these devices can be introduced into the vascular system. Failure to evacuate the air contained within this channel predisposes the patient receiving the procedure to the risk of an air embolism in the event of a balloon rupture. In addition, air contained within the hydraulic channel compromises the hydraulic function of these devices. In general, the hydraulic channel of a conventional "over-the-wire" catheter is sealed at the distal end. Preparation of this channel requires a two-step process. First, the air contained within the hydraulic channel must be evacuated. This is generally accomplished by applying a syringe to the proximal end of this channel and aspirating the contents. Next, the channel must be filled with dilute contrast medium (the universal hydraulic fluid used in conjunction with dilatation balloon catheters). The introduction of contrast media in the setting of incomplete evacuation results in the entrapment of air within the distal aspect of the hydraulic channel (e.g., within the confines of the balloon) and the creation of an air bubble.

The ease with which an air bubble can be removed from the balloon following the introduction of contrast relates directly to the dimensions of the hydraulic channel. It is substantially more difficult to remove air bubbles from smaller profile channels relative to larger profile channels. As a result, "miniaturized" low profile catheters with low profile hydraulic channels are prone to air entrapment. This circumstance has been offset by the development of a variety of air vents that can be installed in the distal aspects of these channels. The function of these vents takes advantage of the fact that the viscosity of a fluid consistently exceeds the corresponding property of a gas.

One example of a vented "over-the-wire" catheter is described in U.S. Pat. No. 4,638,805. In this example, a small passageway is provided from the lumen of the balloon to the tip of the catheter. The passageway is formed by placing a very small diameter wire between the distal aspect of the balloon and the central column within the balloon that contains the guidewire. When the catheter is manufactured, the balloon and the central column are heat-shrunk together with the wire in place. The wire is later removed to allow a small passageway for the exit of air from the balloon during filling of the balloon. By making the passageway sufficiently small, fluid may be retained within the balloon while air is expelled therefrom.

U.S. Pat. No. 4,811,737 describes an alternative method for venting an "over-the-wire" catheter. This patent describes a catheter with a small slit in the exterior surface of the balloon. When fluid is introduced into the balloon, air is forced out of the small slit. The inflation fluid is sufficiently viscous to prevent its escape through the same slit. Unfortunately, the slit creates a region in the surface of the balloon which is prone to failure. When the balloon is inflated to pressures of many atmospheres, the stresses are concentrated at the ends of the slit, making it prone to rupture.

U.S. Pat. No. 4,821,722 describes the use of micromachined openings in the central shaft and balloon surface for the purpose of selectively venting air from the hydraulic channel of an "over-the-wire" dilatation balloon catheter. The openings are sufficiently large to allow the flow of gas therethrough, and yet sufficiently small to prevent the inflation fluid from escaping from the confines of the hydraulic channel.

With respect to the seventh issue, enhanced balloon fragility, polyethylene terephthalate, or PET, is currently being used with increasing frequency to construct the balloon components of low profile catheters. PET is a remarkable material with profound tensile strength. Its use permits the construction of particularly thin-walled balloons capable of withstanding high pressures without rupture. However, this material is particularly fragile and prone to the development of pin-hole tears in response to the usual "wear and tear" that transpires during the course of a routine angioplasty procedure. The development of a pin-hole tear predisposes balloons manufactured with this material to the development of rupture at low pressures. Hence, its use permits the construction of lower profile balloons, in the deflated state, because it can be rendered particularly thin and suitably tolerant to the pressures generated during the course of an angioplasty, and yet its use has been associated with an increased incidence of balloon rupture.

With respect to the eighth issue, reduced balloon profile, a direct relationship exists between the inflation and deflation balloon profiles because dilatation balloons must be constructed with the use of relatively non-compliant materials. Hence, the lower profile catheters commonly carry lower profile balloons. The use of these low profile devices frequently provides incomplete dilatation of the stenosis and thus obligates the use of subsequent catheters, containing larger profile balloons. The performance of a catheter exchange and the use of multiple catheters have been shown to enhance the risk associated with the performance of an angioplasty.

Given the limitations intrinsic to the process of "miniaturization," the fundamental design of the "over-the-wire" catheter was reconfigured with the aim to further reduce the profile and yet circumvent some of the limitations inherent to this process. This effort resulted in the generation of the three additional classes of systems/devices mentioned previously: (1) the "semi-movable" catheter/guidewire composite systems; (2) the "fixed-wire" catheter/guidewire composite systems; and (3) the "balloon-on-a-wire" devices. The design of "semi-movable" and "fixed-wire" systems permits manufacture of these devices with lower profiles relative to "over-the-wire" systems because the guidewire, permanently contained within the confines of these systems, can be rendered lower in profile, relative to the profiles of stand-alone guidewires used in conjunction with "over-the-wire" systems. As in the case of "over-the-wire" systems, these devices contain two separate shaft lumens. The lumen of the guidewire channel in these devices is lower in profile relative to the profile of the guidewire channel contained within "over-the-wire" systems of the prior art. The design of "fixed-wire" systems permits manufacture of these devices with lower profiles relative to "semi-movable" systems because these devices do not contain a central tubular shaft. The guidewires contained within these devices are used to provide column strength for the balloon components. The design of "balloon-on-a-wire" systems permits manufacture of these devices with a lower profile relative to "fixed-wire" systems because the guidewires comprise the shafts of these devices.

Although these designs permit the manufacture of balloon delivery systems with lower profiles relative to "over-the-wire" systems, there exist several functional disadvantages inherent to the designs of these devices. To begin, none of these systems permit separation of the guidewire components from the balloon components and none of these systems accept exchange wires. Hence, the use of these devices obligates removing the guidewire component and sacrificing intraluminal access in the event that a catheter exchange is required.

"Semi-movable devices" provide infinite guidewire rotational mobility. However, they provide limited guidewire/catheter coaxial mobility relative to "over-the-wire" systems. These devices also provide compromised guidewire torque delivery and hence compromised "steerability" because the guidewires contained within these systems are lower in profile relative to "over-the-wire" devices. Finally, the guidewires contained within these devices are more prone to buckling and kinking during introduction across critical stenoses relative to stand-alone guidewires used in conjunction with "over-the-wire" systems.

"Fixed-wire" systems provide less guidewire mobility and deliver less rotational torque relative to "semi-movable" systems. As a result, they provide significantly compromised "steerability" relative to "semi-movable" systems. For example, these devices do not permit coaxial guidewire mobility. Furthermore, they provide only limited rotational mobility. Both of these features relate directly to the fact that the guidewires of these devices are immovably bonded directly to the distal aspects of the balloon catheter components of these systems. This bond permits the guidewire to provide column strength for the balloon and hence constitutes a fundamental component of these devices. And yet, it is because of this bond that the guidewires cannot be advanced or withdrawn in a coaxial direction relative to the catheter components of these devices. It is because of this bond that the guidewires cannot be independently rotated within the confines of these devices. In fact, uni-directional rotation of these guidewires results in progressive wrapping of the balloon components. For this reason, these devices commonly contain torque limiters, as described in U.S. Pat. No. 4,664,113. These torque limiters prevent the operator from over-rotating the guidewire component relative to the catheter component of these systems. Over-rotation of the guidewire can result in stress between the balloon and the guidewire, causing damage to one or both components. Unfortunately, the presence of a torque limiter complicates the angioplasty procedure by requiring the operator to periodically stop the procedure and unwind the guidewire to its "home" position as the operator navigates the catheter through the convoluted arteries of the patient's cardiovascular system.

The presence of this bond, between the guidewire and the distal aspect of the balloon, further compromises the guidewire torque delivery because much of this torque becomes absorbed by the obligate rotation of the balloon component of these devices. In this regard, the balloon can become "hung up" on the luminal surface of a blood vessel. Because rotation of the guidewire requires rotation of the balloon component of these devices, this circumstance dramatically compromises the torque delivery of these devices and hence significantly compromises the "steerability" of these devices within the confines of stenotic lesions.

This practice of bonding the guidewire to the distal aspect of the balloon predisposes to the development of fractures within the segments of the guidewires contained within the balloon components of these devices. These guidewire components are responsible for the delivery of torque to the distal aspect of these devices. Torque delivery is required for directional control. Rotation of these devices subjects these thin and particularly fragile guidewire segments to considerable torsion. The application of excessive rotational force can provoke fractures within the guidewires, a circumstance that commonly transpires when the balloon components become "hung up" within these confines of atheromatous lesions. This circumstance impairs the rotational mobility of the balloon, which, in turn, compromises the rotational mobility and hence directional control of the entire device. This circumstance is commonly met with the application of excessive rotational force. And this response leads to the generation of considerable torsion within the delicate intraluminal guidewire. In the event that the balloon component remains tethered within the confines of the vasculature, then the torsion applied to the guidewire steadily increases with the application of additional rotational torque, until the device eventually fractures.

U.S. Pat. No. 4,715,378 describes a vented "fixed-wire" device. In this patent, a winding passage extending through the bond between the guidewire coil and the distal aspect of the catheter functions as a vent. This device does not appear to have a torque limiter and hence it is prone to over-wrapping with possible rupture of the balloon and fracture of the guidewire.

U.S. Pat. No. 4,793,350 describes another approach for venting a "fixed-wire" device. In this patent, a vent is formed by providing a small space between the guidewire and the distal aspect of the balloon. The catheter and guidewire are fastened together at the distal aspect of the balloon and this device contains a torque limiter.

"Balloon-on-a-wire" systems provide no mobility between the guidewire and the balloon components of these devices. In effect, the balloons on these devices are bonded both proximally and distally to the guidewires. Directional control of these devices is provided by rotation of the entire device. As in the case of "fixed-wire" devices, the practice of immovably bonding the balloons onto the guidewires of "balloon-on-a-wire" devices compromises torque delivery. As in the case of "fixed-wire" devices, this practice predisposes these devices to the development of fractures within the components of the guidewires that span the lumens of these balloons. Tip fracture currently constitutes the fundamental limitation of prior art "balloon-on-a-wire" systems and recently resulted in the FDA recall of the most popular prior art device of this functional class.

SUMMARY OF THE INVENTION

This invention relates to the use of a relatively fluid-tight seal for catheters. The seal consists of a plurality of surfaces that are independently movable relative to one another. The invention has application to the construction of catheters, particularly medical interventional catheters, such as balloon dilatation catheters, (percutaneous transluminal coronary dilatation catheters, peripheral vascular transluminal dilatation catheters, valvuloplasty catheters, intra-cranial intra-vascular dilatation catheters, genito-urinary dilatation catheters,) laser ablation catheters, fiber-optic intra-vascular catheters, rotational ablation catheters, intra-aortic balloon dilatation catheters, and atherectomy catheters. In addition, the invention has application to the construction of composite catheter systems (e.g., guiding catheter/dilatation balloon systems, laser delivery/dilatation balloon systems, atherectomy/dilatation balloon systems, intravascular ultrasound/dilatation balloon systems, angioscopy/atherectomy systems, angioplasty dilatation balloon/guidewire systems, including "semi-movable," "fixed-wire" and "balloon-on-a-wire" systems, etc.).

According to the invention, a seal can be created by the precise juxtaposition of two or more independently movable surfaces. The seal is sufficiently fluid-tight for most interventional catheters. The effectiveness of this seal depends upon: (1) the proximity of the two surfaces that comprise the interface, (2) the surface area common to the interface, (3) the pressure differential applied across the interface, and (4) the viscosity of the fluid contained by the interface.

The use of a seal of this nature in the construction of catheters and catheter systems permits the generation of relatively fluid-tight channels with surfaces that are movably disposed relative to one another, and the generation of relatively fluid-tight channels that contain structures that are movably disposed relative to the channels themselves. The use of this seal in the construction of catheters (or catheter systems) circumvents the need to separate hydraulic channels from other channels containing components (e.g., guidewires, etc.) that are movably disposed relative to the particular catheter (or catheter system). This feature permits the construction of catheters in general and "over-the-wire" and "semi-movable" systems in particular, with fewer channels. Thus, the process of catheter manufacture is simplified. Additionally, the development of catheters and catheter systems with smaller shaft dimensions and/or larger hydraulic channel dimensions is made possible, enabling superior hydraulic performance characteristics relative to conventional catheters and systems.

The use of a seal of this nature in the construction of "fixed-wire" and "balloon-on-a-wire" catheter systems further permits the manufacture of these devices with enhanced mobility of the balloon components relative to the guidewire components of these systems. This can be accomplished because the use of our seal, in conjunction with a means of providing column support for the balloon components of these devices that does not compromise the rotational mobility of the guidewire relative to the balloon, permits the construction of these devices with infinite guidewire rotational mobility relative to the balloon component and yet preserves hydraulic competence. This intercomponent rotational mobility, in turn, permits the construction of these devices with enhanced torque delivery, enhanced directional control and diminished propensity for balloon rupture or guidewire fracture, relative to the prior art.

The use of a relatively fluid-tight seal consisting of a plurality of surfaces that are independent and movable relative to each other is a profound departure from convention. Adhesives and or other bonds are almost universally used in the creation of conventional seals, a practice that clearly does not permit the independent movement of the component surfaces that converge in the region of these seals. Although the seal described herein has application to any medical catheter that contains a hydraulic channel, below we focus on the application of this seal to the construction of dilatation balloon catheters. The benefits afforded by the incorporation of this seal into the construction of these catheters will become evident from the following text and figures.

BRIEF DESCRIPTION OF THE DRAWINGS

FIGS. 1A-1B illustrate a conceptual view of our invention.

FIGS. 1C-1H illustrate embodiments of the invention in various configurations in catheters.

FIGS. 2A-2E and 2E' illustrate multiple views of a prior art "over-the-wire" angioplasty dilatation balloon catheter.

FIGS. 2F-2I illustrate an intra-vascular catheter system containing a relatively liquid-tight seal at each end of the catheter.

FIG. 2J illustrates a prior art catheter cross section.

FIGS. 2K-2O illustrate cross-sectional profiles of various embodiments of our invention.

FIGS. 3A-3H illustrate "over the wire" catheter systems where the seal is used solely as a vent.

FIGS. 4A-4M illustrate "over the wire" catheter systems where portions of the central shaft are removed.

FIGS. 5A-5G illustrate catheters which can be withdrawn over a guidewire, but do not permit the reintroduction of a guidewire.

FIGS. 6A-6G illustrate additional catheters which can be withdrawn over a guidewire, but do not permit reintroduction of a guidewire.

FIGS. 7A-7H illustrate a series of "semi-movable" dilatation balloon catheter/guidewire systems.

FIGS. 8A-8F illustrate a series of "fixed-wire" dilatation balloon catheter/guidewire systems.

FIG. 9A is a side view of the proximal portion of a prior art dilatation balloon catheter coupled to a Y-adapter.

FIGS. 9B-9G illustrate proximal portions of catheters where the catheter employs our seal.

FIGS. 10A-10E illustrate a series of guidewire configurations useful in conjunction with catheters shown in other figures.

FIGS. 10F-10P illustrate a series of "balloon-on-a-wire" systems.

FIG. 11A illustrates a conventional complete balloon angioplasty catheter system.

FIGS. 11B-11G illustrate the applicability of seals of our invention to the construction of composite catheter systems.

DETAILED DESCRIPTION OF THE PREFERRED EMBODIMENT

Overview of Our Seal

The following describes several new catheter designs that permit the construction of dilatation balloon catheters of lower profile and superior performance characteristics relative to conventional catheters. An important feature of each catheter design is a relatively fluid-tight seal that consists of a plurality of independently movable surfaces.

The use of our invention to achieve low profile affords multiple advantages relative to the prior art approach of miniaturization. For example, the use of our seal permits the construction of "over-the-wire" and "semi-movable" dilatation balloon catheter systems with lower profile, and yet superior "pushability," hydraulic performance, guidewire compatibility, and guidewire torque delivery relative to the prior art. Finally, our approach provides an advantage in catheter construction that will endure the advent of new manufacturing techniques and new synthetics, developed with the aim to reduce conventional catheter profiles and enhance performance because many of these advancements can be applied to the manufacture of the catheters described herein.

The use of our seal further permits the construction of "fixed-wire" and "balloon-on-a-wire" catheter systems with superior guidewire rotational mobility, guidewire torque delivery, directional control and diminished propensity for balloon rupture or guidewire fracture, relative to the prior art. This can be accomplished because the use of our seal, in conjunction with a means for providing column support for the balloon components of these systems which does not limit the rotational mobility of the guidewire relative to the balloon, permits the construction of these devices with infinite guidewire rotational mobility relative to the balloon and yet preserves the hydraulic competence. Additionally, the use of our seal in the construction of "fixed-wire" systems circumvents the need to include torque-limiters in the construction of these devices.

Finally, the use of our seal provides an air vent for the hydraulic channels of "over-the-wire," "semi-movable," "fixed-wire" and "balloon-on-a-wire" devices.

As shown in FIG. 1, particularly FIGS. 1B-1G, a relatively fluid-tight seal can be created by the precise juxtaposition of two (or more) reciprocal surfaces. FIG. 1A illustrates the use of a seal consisting of two surfaces 5 in proximity, to contain a liquid within a bath. The competence of this seal is a function of at least the following parameters: the degree of separation S between the two (or more) surfaces 5 that comprise the interface, the surface area common to the interface, the viscosity of the fluid contained by the interface, and the pressure differential applied across the interface. In general, the competence of the seal is directly related to the common surface area and fluid viscosity and inversely related to the degree of separation, and the pressure differential.

Although depending upon manufacturing tolerances leakage may be inevitable with a seal of this design, a seal can be constructed in this manner that provides sufficient fluid retention to meet the functional requirements of interventional catheters. In general, interventional catheters are prepared with contrast media, a particularly viscous fluid that is relatively easily contained by a seal of this nature.

In the preferred embodiment, the components of this seal are movably disposed relative to one another, and the seal itself is selectively fluid-tight, but typically not air-tight. Both of these requirements can be satisfied by providing the proper separation between the two surfaces that comprise the interface. In effect, the surfaces that comprise the seal must be positioned sufficiently close together to create a fluid-tight seal, and yet sufficiently far apart to permit the passage of air and free movement of the components. The selectivity of the seal takes advantage of the fact that the viscosity of a fluid consistently exceeds the corresponding property of a gas.

Preferably, the seal is composed of materials that are relatively noncompliant and that accept a smooth surface. In the preferred embodiment, the surfaces common to the interface are smooth. Of course, by extending the length of the sealing surfaces, increasing roughness can be tolerated. Malleable materials or inflatable components can be used to create seals that are fluid-tight. The use of these materials/components, however, in the construction of fluid-tight seals requires the use of compression to maintain the competence of the seal. This circumstance invariably results in the generation of friction between the surfaces common to the seal.

A functional seal of this nature can be created by the juxtaposition of any two surfaces, of virtually any configuration, that have a sufficient surface area in common. (See FIGS. 1B-1F.) In the preferred embodiment, the interface consists of a rod 6 contained within a sleeve 7, as shown in FIG. 1B. This configuration permits the construction of an interface with elements that are both slidably and rotatably movable relative to one another.

Although alternative designs exist, they do not provide commensurate inter-component mobility. Nonetheless, these designs could be used in the construction of catheter systems wherein it would be desirable to install a seal of our design that does not provide full rotational and/or coaxial mobility. For example, a configuration of our seal that provides full rotational mobility and yet no coaxial mobility between the composite surfaces of the seal, could be used in the construction of "fixed-wire" and "balloon-on-a-wire" devices. Some of these designs are discussed below. The design illustrated in FIGS. 1D and 1D permits the construction of an interface consisting of two independent structures that are slidably movable relative to one another, and yet not rotatably movable relative to one another. The design illustrated in FIGS. 1E and 1E' permits the construction of a seal consisting of two independent structures that are rotatably movable and yet not slidably movable relative to one another. The design illustrated in FIGS. 1F and 1F' permit the construction of a seal consisting of two independent structures that are rotationally, and yet not slidably disposed relative to one another. The design illustrated in FIGS. 1G and 1G' and 1H and 1H' permit the construction of seals consisting of two independent structures that are rotatably and yet not slidably disposed relative to each other. Additionally, the competence of these latter seals (e.g., FIGS. 1F-1G) requires the application of a force, commensurate with the opposing force created by the pressurized fluid contained therein, to maintain the competence of the seal 1.

The seal of this nature can be installed at any seal point 1 along the length of the catheter, as illustrated in FIG. 1C. In the upper portion of FIG. 1C, a seal point 1 is shown at both the distal and proximal ends of the catheter and includes a smooth portion (shown clear) of the guidewire 80. In the middle portion of FIG. 1C a seal point 1 is disposed intermediate within the shaft near the balloon. Finally, in the lower portion of FIG. 1C, a seal point 1 is formed both at the distal end between the balloon and the guidewire and within the catheter shaft between the outer wall of the shaft and the guidewire, enabling the guidewire to exit the catheter wall.

In each of the portions of FIG. 1C, the seal is shown as being formed between a smooth region of the guidewire 80 and some other portion of the catheter. It should be understood that the length of the smooth portion of the guidewire shown in FIG. 1C (and in all the other figures herein) is merely for the purpose of illustration. In particular, the smooth portion of the guidewire may be extended as necessary to provide a seal over a longer range of movement. For example, in the upper portion of FIG. 1C, the seal 1 at the distal aspect of the balloon portion 50 of the catheter is shown as approximately 1 cm. in length. In some embodiments of the invention, the seal may extend over a considerably longer portion of the length of guidewire 80, depending primarily upon the extent to which it is desired to advance guidewire 80 beyond the distal tip of the balloon. For example, if it is desired to advance guidewire 80 20 cm. beyond the tip of the balloon, then about 20 cm. of the guidewire will be rendered smooth.

A suitable interface according to our invention can be constructed with a sleeve about 0.5 cm in length containing a smooth rod approximately 0.008 to 0.010 inches in diameter separated from the sleeve by 0.001 to 0.0001 inches. This embodiment permits the passage of air, permits the independent movement of both structures relative to one another, and yet contains 25% contrast media when subjected to a pressure of 10 atmospheres for more than 2 minutes without a significant fall in pressure or loss of fluid. Angioplasty procedures are generally accomplished with lower pressures and shorter balloon inflation times. Thus, the seal created by our interface is highly advantageous for use in the construction of angioplasty dilatation balloon catheters.

In our preferred embodiment we use polyimide and stainless steel to manufacture the seal components. Both polyimide and stainless steel can be manufactured to particularly high tolerances and thus are well suited for the construction of the interface described herein. Each material can be rendered into rods or particularly thin-walled tubular segments. Because polyimide is more resilient relative to stainless steel, and hence less prone to develop kinks, we typically employ a stainless steel rod surrounded by a polyimide sleeve, although other implementations are also satisfactory.

The construction of our seal, however, is not limited to the use of these materials. In fact, any biologically compatible material that can be manufactured with sufficient tolerances to meet the requirements described herein can be used in the construction of the components of this interface. Below for clarity, we refer to stainless steel and polyimide in the construction of the seal, but with the understanding that the manufacture of our seal is not limited to these two materials alone.

Satisfactory stainless steel and polyimide components can be purchased from precision vendors. It should be recognized, however, that a variety of methods can be used to construct reciprocal components of an interface, including heat shrinking, potting, precision injection molding, and high tolerance extrusion. Finally, in some embodiments a biologically compatible lubricant will be applied to the common surfaces of the interface to provide a seal that is both fluid-tight and air-tight.

The seal described herein can be used to create a relatively fluid-tight seal between any two or more structures that are movably disposed relative to one another within individual catheters or catheter systems. For example, as shown in FIG. 1 the interface described herein can be used to create a fluid-tight seal between the catheter and the guidewire installed therethrough. In this circumstance, the central component 6 (see FIG. 1B) of the seal will consist of a segment of the guidewire that has been rendered smooth, while the peripheral component 7 will consist of a segment of thin-walled polyimide tubing that has been bonded to the luminal surface of the catheter component of the system.

The development of a satisfactory seal between the guidewire and catheter requires a smooth surface on the guidewire in the region of the seal, which surface conforms to the luminal surface of the polyimide sleeve. In general, the distal surfaces of guidewires of the prior art are not smooth; hence these devices must be modified accordingly. A variety of methods can be used to create guidewires that contain distal segments with uniform surfaces. In the figures a white zone is used to indicate the segment of the guidewire that has been rendered smooth.

Although the manufacture of the interface requires precision, it should be recognized that contrast media, the fluid commonly used to transmit hydraulic pressure within interventional catheters, is relatively viscous and hence relatively easily contained by a seal of our type. Hence, minor imprecision will not affect the competence of the seal, enabling seals of this nature to be constructed with mass production techniques.

The following discussion provides a perspective concerning the value of our seal in the construction of "over-the-wire" and "semi-movable" dilatation catheters. Although we focus in this section on the use of this seal in one particular "over-the-wire" catheter, it should be recognized that this seal has application to the construction of an entire series of devices. Additional advantages of this seal will become evident from the examples discussed.

FIG. 2F is a side view of an intra-vascular "over-the-wire" dilatation balloon catheter/guidewire system of our design that contains two relatively liquid-tight seals 1 disposed at each end of the catheter. FIG. 2G is an enlarged view of the distal aspect 50 of the same device. FIG. 2H is an end view of the same, while FIG. 2I is a cross-sectional view of the shaft of the device. In this example, the guidewire 80 functions as the central component 6 of each seal 1. It is movably disposed within two polyimide sleeves 7 that have been bonded to the singular luminal surface of the catheter at opposite ends of the device.

The catheter of our invention represents a significant departure from conventional catheters that provide unrestricted guidewire movement because the shaft is composed of a singular tube 66. The use of the liquid-tight interface 1 and a means of providing column strength for the balloon that is independent of the guidewire circumvents the need to include in the construction of our "over-the-wire" and "semi-movable" catheters a central tube 44 that extends the length of these devices typified by the prior art catheter of FIG. 2A-2E. The central tubular component 44 of conventional "over-the-wire" and "semi-movable" catheter performs two functions. First, it affords column strength to the "balloon-like" component 52 of these catheters. Second, it separates the two functionally distinct channels 42,46 that extend the length of these catheters. As shown in FIGS. 2F-2I and 2K-2O, the use of interface 1 in catheters of our design permits the construction of catheters that contain singular multipurpose channels 64 which accommodate guidewires 80 movably disposed therein, while at the same time convey hydraulic pressure along the length of these devices. Hence, the use of this seal eliminates the need to provide separate channels. Furthermore, balloon column strength can be provided in a number of ways that do not require the use of a central tube extending the length of the catheter. We provide column strength for many of our catheters without relying upon this approach. Thus, the use of our seal and alternative methods for providing balloon column strength permit the partial or complete removal of the central tubular element.

Partial or complete elimination of the central tubing 44 permits the construction of a variety of "over-the-wire" or "semi-movable" catheter systems with a variety of combinations of shaft and hydraulic channel profiles that are superior to conventional catheters. (See FIGS. 2K-2O.) FIG. 2J is a cross-sectional view of a prior art low profile catheter shaft for reference. FIG. 2K illustrates the corresponding view of the shaft of the catheter of our design with the same shaft profile. Note that the cross-sectional area of the hydraulic channel 64 contained within this device is substantially larger than that corresponding area 46 of the prior art device of similar shaft profile. Given the relationship between the inflation/deflation rate and the cross-sectional profile of the hydraulic channel, the removal of the central tubing component 44 permits the construction of low profile "over-the-wire" and "semi-movable" catheters with substantially faster inflation/deflation rates and shorter inflation/deflation cycle time relative to the prior art. Thus, our seal can be used to construct "over-the-wire" and "semi-movable" catheter guidewire systems with faster inflation/deflation rates and hence superior hydraulic performance relative to prior art devices of the same external catheter shaft dimensions. Hence, the use of our seal can be used to create catheters that permit less interruption of blood flow at the beginning and end of the dilatation phase of coronary angioplasty.

In this regard, it is believed that the use of this seal can permit the development of catheters that provoke minimal interruption to blood flow throughout the dilatation phase of the procedure as well. It is known that blood flow within the coronary circulation varies dramatically throughout the cardiac cycle. Virtually all blood flow within the arterial circulation of the heart occurs during diastole, the phase of the cardiac cycle during which cardiac relaxation transpires. In contrast virtually no blood flow occurs during systole, the phase of the cardiac cycle during which cardiac contraction transpires. If a catheter permits relatively normal blood flow during diastole, and permits inflation and deflation of the balloon component within the time frame of the cardiac cycle (e.g., 0.5-1.5 seconds), then it is expected that such a catheter will permit the performance of pulsatile angioplasty (with balloon inflations limited to systole), thereby permitting coronary perfusion during the dilatation phase of the procedure. At present, the inflation/deflation cycle time for conventional low profile catheters prepared with 25% contrast media ranges between 8-12 seconds. Convention requires balloon-mediated plaque distention for a period of 60-90 seconds in the performance of an angioplasty. Given the limitations of current technology, this is usually accomplished by inflating the balloon for 60-90 seconds at a time, a circumstance that invariably provokes profound ischemia.

Thus, catheters employing our invention minimize the interruption in blood flow to the heart in two ways—first by enabling the use of smaller profiles than heretofore possible, and second by providing enhanced hydraulic performance during inflation/deflation procedures.

FIG. 2L illustrates a low shaft profile version of the catheter of our design with a hydraulic channel cross-sectional area that is commensurate with convention. FIG. 2M illustrates a catheter shaft of our design with a lower overall profile and larger hydraulic channel cross-sectional area relative to convention. FIG. 2N illustrates the cross-sectional appearance of the shaft and guidewire of a monorail version of our design (illustrated in profile in FIG. 4J).

Removing the central tubular component also permits the construction of high performance, low profile "over-the-wire" and "semi-movable" catheters and/or catheter systems that have enhanced pushability. If the singular tubular component of this shaft has a wall thickness that exceeds conventional wall thickness, then this objective is accomplished, provided that the compliance of the material used in the construction of the catheter is commensurate with convention (see FIG. 2O).

The use of our seal further permits the construction of "over-the-wire" and "semi-movable" angioplasty dilatation balloon catheter systems with enhanced guidewire torque delivery, superior "steerability," and superior guidewire compatibility, relative to the prior art. This seal permits the construction of these devices with single multi-purpose channels that are significantly larger in cross-sectional profile relative to the guidewire channels contained within corresponding prior art devices that have commensurate external catheter shaft dimensions. Hence, this seal permits enlargement of the channels that contain the guidewires in our devices. This feature, in turn, minimizes the friction that develops between the guidewire and the luminal surface of the catheter guidewire channel during the process of rotating the guidewire within devices of our design. This feature enhances the efficiency of guidewire torque delivery within the confines of the "guidewire" channel of "over-the-wire" and "semi-movable" systems of our design, relative to the prior art. In addition, this feature enables the construction of very low profile catheters that accommodate larger profile guidewires relative to prior art "over-the-wire" and "semi-movable" catheters of commensurate external shaft profile. Because these larger guidewires provide superior directional control and stability relative to smaller profile wires, this feature further enhances the "steerability" of "over-the-wire" and "semi-movable" catheters of our design relative to the prior art.

The use of our seal further permits the manufacture of "over-the-wire" and "semi-movable" catheters with superior trackability relative to the prior art. Trackability varies as a function of: (1) the resistance generated between the guidewire and guidewire catheter lumen during coaxial movement of the catheter relative to the guidewire, and (2) the flexibility of the catheter component of the system. The use of our seal permits the construction of "over-the-wire" and "semi-movable" systems with larger profile guidewire lumens relative to the prior art. And this circumstance reduces the extent to which the guidewires contained within these devices contact the luminal surfaces of the catheter shafts during coaxial movement of the catheters relative to the guidewires. Furthermore, the use of our seal circumvents the need to provide separate channels within the shafts of "over-the-wire" and "semi-movable" devices, and this feature permits the construction of catheter shafts of devices that employ our seal with fewer walls and hence enhanced flexibility relative to the prior art.

Both of these features enhance the trackability of devices that employ our seal.

The use of our seal also permits the construction of "fixed-wire" and "balloon-on-a-wire" devices that do not contain an immobile bond between the balloon and guidewire components of these devices. The use of our seal in conjunction with a means for providing column support for the balloon components of these devices that does not limit the rotational mobility of the guidewire relative to the balloon, permits the construction of these devices with infinite guidewire/balloon component rotational mobility. In other words, this approach permits the manufacture of "fixed-wire" and "balloon-on-a-wire" systems that contain guidewires which can be rotated independent of the balloon components of these systems. This feature permits the manufacture of these devices with markedly enhanced guidewire mobility, torque delivery and "steerability," relative to the prior art. This feature further permits the manufacture of "fixed-wire" and "balloon-on-a-wire" devices that are significantly less prone to the development of balloon wrapping, guidewire fracture and wrapping-mediated balloon rupture relative to the prior art. This approach further eliminates the need for a torque limiter in the manufacture of "fixed-wire" devices.

The use of our seal further permits the selective evacuation of air contained within the hydraulic channels of "over-the-wire," "semi-movable," "fixed-wire" and "balloon-on-a-wire" systems consequent with the process of preparing these devices with contrast medium. Because our seal is selectively fluid tight and not air tight, it is entirely suited for this purpose. The use of our seal circumvents the need to apply a vacuum to the hydraulic channels of these devices prior to the introduction of contrast medium. Hence, the use of our seal permits the manufacture of catheters that are easier to prepare for insertion into the body relative to corresponding prior art unvented devices.

Thus, the use of our seal permits the manufacture of "over-the-wire" and "semi-movable" systems with lower profile, superior hydraulic performance, superior guidewire torque delivery, superior guidewire compatibility, superior trackability, superior flexibility and superior pushability relative to the prior art. In addition, the use of our seal permits the manufacture of "fixed-wire" and "balloon-on-a-wire" devices with enhanced torque delivery, and steerability relative to the prior art, that are significantly less prone to the development of wraps within the balloon, guidewire fracture, and wrap-mediated balloon rupture. The use of our seal further eliminates the need for "torque-limiters" in the manufacture of "fixed-wire" devices. Additionally, the use of our seal provides a vent for the hydraulic channels of devices of each of the aforementioned functional classes. Below we discuss a series of designs for "over-the-wire," "semi-movable," "fixed-wire" and "balloon-on-a-wire" systems, as well as systems that contain our seal that do not conform to any current functional category.

FIGS. 3–8 include side views of the distal portions of a variety of dilatation balloon catheters that can be constructed with the use of our interface. The devices have been grouped together according to functional class.

FIGS. 3 and 4 illustrate "over-the-wire" catheter systems of our design.

FIGS. 5 and 6 illustrate a series of devices that can be withdrawn over the guidewire, but do not permit the reintroduction of a guidewire. Hence, if a catheter exchange is anticipated, catheters of this type must be used in conjunction with exchange wires. The performance of a catheter exchange with one of these devices prepared with a standard (e.g., non-exchange) wire, requires sacrificing intra-luminal access to accomplish this procedure.

FIG. 7 illustrates a series of "semi-movable" systems of our design.

FIG. 8 illustrates a series of "fixed-wire" devices of our design.

FIG. 9 illustrates a series of proximal adapters that can be used in conjunction within the aforementioned catheter systems.

FIGS. 10A–10C illustrate several alternatives for the construction of guidewires, for use in conjunction with the aforementioned "over-the-wire" catheters, that contain segments with a smooth surface.

FIG. 10D is an off-center inset of the wire contained with "semi-movable" and "fixed-wire" devices of our design.

FIG. 10E illustrates an enlarged profile view of the guidewire contained in FIG. 10D.

FIGS. 10F–10I illustrate a series of "balloon-on-a-wire" devices of our design.

FIG. 11 illustrates the use of our seal in the construction of a very low profile, guiding catheter/dilatation balloon catheter/guidewire system. This allows a ultra-low profile multi-catheter system that contains hydraulically competent channels. Although the system must be modified to accommodate alternative devices, e.g., atherectomy devices, etc., it should be evident that the use of a fluid-tight seal consisting of a plurality of independently movable surfaces has particular application to the construction of composite catheter systems.

SPECIFIC EXAMPLES

FIG. 3A–3F illustrate the use of our seal 1 as an air vent for the hydraulic channels of over-the-wire dilatation balloon catheters that have relatively conventional catheter shafts. Because the seal is selectively fluid-tight, and not air-tight, it is well suited for this purpose. Unlike the vents described in U.S. Pat. No. 4,821,722, the vents described in FIG. 3 do not rely upon the size of the hole in the central shaft for selective fluid retention. Rather, the interface between the guidewire and the central shaft functions selectively to permit the passage of air and retain fluid in the case of the catheters of our design. This circumstance renders our vents easier to manufacture relative to the vents described in U.S. Pat. No. 4,821,722. Our design functions with the use of holes in the central tubing that are large enough to permit the passage of fluid. The vents described in U.S. Pat. No. 4,821,722 rely upon the size of the holes formed in the central tubing for selectively. Hence, the approach described in U.S. Pat. No. 4,821,722 mandates the creation of extremely small holes in the central tubing. Unfortunately, the material used in the construction of the central shafts of prior art devices is relatively flexible and hence, not particularly amenable for use in the construction of precision holes. In short, the vents described herein are functionally distinct and easier to manufacture relative to the prior art means of venting the central shaft.

The use of a seal that is relatively fluid-tight and yet not air-tight greatly expedites the process of catheter preparation. Such a seal permits evacuation of the air contained within the hydraulic channel consequent with the introduction of contrast, eliminating the need to establish an apriori vacuum within this channel. It also permits the evacuation of air trapped in the balloon following preparation of the device.

FIG. 3A illustrates a device that contains a fenestration 73 within the central tubular component of the catheter shaft 44 to permit the evacuation of air through a fluid-tight interface 1. When the balloon is filled prior to use, air can escape through the tip of the catheter. The vent consists of: (1) a smooth segment 82 of the guidewire 80 that is movably contained within a polyimide sleeve, and (2) the polyimide sleeve that is bonded to the luminal surface of the central tubular component 44 of the catheter shaft. A laser can be used to create a fenestration within the polyimide.

FIGS. 3B-3E depict various embodiments of this basic catheter design. FIG. 3B illustrates the use of a sleeve of polyimide tubing with multiple fenestration in the construction of a segment of the central tubular component of the device. FIG. 3C illustrates an off-center view of the same device. FIG. 3D illustrates the use of a fenestrated segment of polyimide tubing 71 that extends the length of the "balloon-like" component of the device. The polyimide tubing 71 replaces the distal portion of the central shaft 44. This design permits the construction of a vented catheter with a lower balloon profile because polyimide can be rendered very thin relative to the materials used in the construction of the central tube of a conventional catheter.

FIG. 3E illustrates the use of polyimide tubing 71 in the construction of the entire central tubular component 44. This approach permits the construction of a vented catheter with a lower profile tip 51, balloon 52 and shaft 40, relative to the prior art.

FIG. 3F illustrates a catheter similar to the device depicted in FIG. 3E, except the fenestration 73 is within the mid-shaft of the device 40.

FIG. 4 illustrates a variety of "over the wire" systems in which the central polyimide tubular component 71 terminates within the shaft 40 of the device. In effect, the devices shown in FIG. 4 contain a single multi-purpose channel 64 throughout most of their length. The proximal end 77 of the central tubing 71 is supported by a plurality of radially disposed structures 75 that extend from the luminal surface of the catheter shaft tubing 66 to the outer surface of the polyimide tubing 71, as shown most clearly in FIG. 4B. These elements, in combination, define a cone type structure that contains spaces which permit the transmission of hydraulic pressure. These spaces, however, are too small to permit the passage of guidewires introduced into the confines of this composite conical structure. In essence, the supporting elements 75 provide column strength to the device and direct guidewires introduced therethrough into the lumen of the polyimide tubing 71 without significantly compromising the hydraulic function of the catheter itself. This is shown most clearly in FIG. 4C. This composite conical structure effectively transmits the column strength of the device from the tubular structure 66 that largely comprises the shaft of the device to the central tubular structure 71 that extends through the balloon to the distal end of the device.

FIGS. 4A-4C illustrate the design of a catheter which contains a polyimide central tubular component that extends into the mid-shaft of the catheter. This design permits the construction of a vented catheter with a faster inflation/deflation rate than the device depicted in FIG. 3F. Relative to the other devices depicted in FIG. 4, this device has a larger profile and is less difficult to construct.

FIGS. 4D-4G illustrate several catheter designs that contain polyimide central tubular components 71 that terminate within the confines of the "balloon-like" component. These designs permit the manufacture of particularly low profile "over-the-wire" dilatation balloon catheter systems because they eliminate the need to overlap the tubular components of the catheter shaft in the construction of these devices. Compared to the device of FIGS. 4A-4C, however, these devices are more difficult to construct, because the supporting cone must be installed within the confines of the "balloon-like" structure.

FIG. 4D illustrates a vented functional device of this design constructed with an imperforate polyimide tube 71.

FIG. 4E illustrates an alternative approach in which a fenestration 73 is provided at the distal end of the central tubular component 71 to provide a vent 73 for the balloon.

FIGS. 4F and 4F' and 4G illustrate the design of a catheter system that permits the construction of a vented dilatation device of lower profile and superior hydraulic performance relative to the prior art, that can be used to inject contrast, blood products, oxygen-carrying blood substitutes or medications into the vascular space distal to the device with higher flow rates relative to the prior art devices. Among the many applications of this device, are delivery of oxygenated blood to regions of the myocardium subserved by vessels that are prone to collapse in the wake of an unsuccessful angioplasty procedure.

Conventional devices of this type are called "bailout" catheters, and are commonly installed across lesions that are prone to collapse during unsuccessful angioplasty procedures. U.S. Pat. No. 4,790,315 describes a prior art "bail-out" catheter. The rate of fluid delivery which can be achieved with conventional devices is limited because the luminal dimensions of the delivery channel are significantly smaller than the corresponding dimensions of the multi-purpose channel of our design. The luminal dimensions of conventional devices closely approximate the outside dimensions of guidewires. In addition, the hydraulic channels of "bailout" conventional devices are separate from the guidewire channels and hence cannot be used to deliver fluid into the vasculature distal to the device.

The catheter depicted in FIGS. 4F and 4G is prepared with a guidewire that contains a segment 81 that does not conform to the luminal surface of the polyimide tubular component 71. Perspective views of two possible configurations for this segment of the wire are shown in FIGS. 4K and 4L. The coaxial relationship of the catheter and guidewire determines the function of the system. FIG. 4F illustrates the alignment of these two components to provide a fluid-tight seal within the distal aspect 51 of the catheter component of the device and to permit inflation of the "balloon-like" component. Advancing the wire relative to the catheter eventually renders the seal entirely incompetent, and permits the escape of the contents of the hydraulic channel (e.g., contrast media, medications or blood products) into the intravascular space containing the device. Removal of the guidewire also renders the seal incompetent and permits the injection of fluid through the device with an enhanced flow rate. Thus, the single channel within this device functions to accommodate the guidewire, transmit hydraulic pressure for inflating the "balloon-like" component, and convey other fluid such as medications, contrast and blood products into the vasculature distal to the device.

The flow rates that can be achieved through our device exceed those possible with conventional devices because the dimensions of the singular hydraulic channel of our device exceed the corresponding dimensions of conventional "bail-out" catheters. In addition, the polyimide tube does not impair flow, because of the multiple fenestrations permitting passage of fluid. The primary limitation to flow through our device is the segment of tubing contained within the extreme distal aspect of the catheter. The dimensions of this component, however, are comparable to the luminal shaft dimensions of the guidewire and hence perfusion channels of conventional "bail-out" catheters.

FIGS. 4H and 4H' and 4I illustrate a catheter system that is similar in function to the device depicted in FIGS. 4F and 4G. In this case, the guidewire 90 contains a lumen 92 that is used to conduct hydraulic fluid via multiple fenestrations 94 variously into the balloon, or distal vasculature, depending upon the coaxial relationship of the guidewire and catheter components of the system.

FIGS. 4J and 4M illustrate a relatively fluid-tight interface 1 in the mid-shaft of a single channel low profile vented "monorail" catheter. The use of our seal permits the guidewire to exit the confines of the singular multi-purpose channel contained within the catheter shaft without disrupting the hydraulic integrity of the system. "Monorail" systems permit manipulation of the catheter independently of the guidewire. Although conventional "monorail" devices exist, these devices have separate lumens for the guidewire and the hydraulic fluid. The guidewire lumen simply terminates within the mid-shaft. U.S. Pat. No. 4,748,982 and U.S. Pat. No. 4,762,129 describe prior art "monorail" systems. The use of our seal permits the construction of "monorail" catheters that do not require separate lumens to convey hydraulic pressure and conduct the guidewire. Hence, the use of our seal permits the manufacture of these devices with lower profiles, superior guidewire torque transmission, superior guidewire compatibility, superior flexibility, superior trackability, and superior hydraulic performance relative to prior art "monorail" devices.

FIGS. 5A-5F illustrate a series of different devices that can be withdrawn over the course of guidewires. These devices, however, will not accept the reintroduction of a guidewire through the entire device.

FIG. 5A illustrates a device that is similar to the device depicted in FIG. 3A. In FIG. 5A, however, the polyimide sleeve that comprises the peripheral component of the interface has been separated into two sleeves, of similar dimensions. One of these sleeves is bonded to the luminal surface of the balloon and the other is bonded to the corresponding surface of the central tubular component of the catheter shaft 44. This configuration permits removal of the central tubular component 44 of the shaft without disrupting the integrity of the hydraulic channel (see FIG. 5B). FIG. 5A' is a perspective off-center view of the catheter showing in more detail the split 77 between the portion of polyimide sleeve 71 attached to the balloon and the portion attached to component 44.

This configuration enables the operator to dispense with the central tubular component 44 of the device once it is no longer required. As indicated previously, the central tubular component provides column strength for the distal segment 50 of the catheter during the process of catheter introduction. Following proper placement of the catheter within the confines of a lesion, however, this component confers little benefit. In fact, it constitutes a limitation to the hydraulic performance of the device. The configuration shown permits the operator to advance the device intact, and then remove the central component. This design permits the manufacture of a high performance, low profile angioplasty device that could be adapted to provide pulsatile dilatation of the balloon component with minimal interruption to blood flow during the inflation phase of the procedure.

FIGS. 5C-5D illustrate cross-section and off-center views of a vented, low-profile, single channel device that does not contain any structure within the confines of the "balloon-like" component that functions to provide column strength for the distal segment of the catheter. Column strength, in this circumstance, derives from the wrapped configuration of the balloon 52, a configuration that can be maintained by the use of reversible bonding agents or other temporary means. The use of our seal in conjunction with reversible bonding permits the complete removal of the central tube 71 and enables the construction of an angioplasty catheter that can be separated from the guidewire contained therein which is lower in profile and more flexible relative to the prior art.

In addition to column strength, the wrapped configuration depicted provides several important advantages. In particular, it provides a compact and streamlined technique for packaging the balloon in its deflated state. In addition, the wrapped condition prevents the development of protrusions within the balloon itself which extend outward from the catheter shaft. (Protrusions typical of the prior art are shown in FIGS. 2E' and 2E.) These protrusions can impede the introduction of the catheter into a region of stenosis. Furthermore, the wrapped configuration of the balloon depicted in FIG. 5D also precludes the development of wrinkles at the junction of the balloon and shaft 66. In short, the use of wrapped configuration and reversible bonding reduces the coefficient of friction of the surface of the balloon component and expedites the passage of the catheter within the confines of a vascular stenosis. The use of reversible wrapping in conjunction with our seal permits the manufacture of an ultra-low profile angioplasty dilatation balloon catheter system with a lower coefficient of friction, superior torque delivery, superior guidewire compatibility, superior guidewire trackability, superior steerability, and superior hydraulic performance relative to prior art devices that permit independent movement of the guidewire.

Typically, the balloon will be distributed in the wrapped configuration, and it will not be unwrapped until it is inflated within the region of stenosis. Also typically the lumen created by wrapping the balloon will be of a sufficient size to permit desired movement and rotation of the guidewire within the confines of the wrapped balloon.

Of course, depending upon the desired column strength for this portion of the catheter, the balloon may be wrapped more tightly or loosely around the guidewire.

The wrapped configuration of the balloon typically is maintained by a temporary bond designed to tolerate the stresses applied to this portion of the catheter during its introduction across a stenosis, and yet release when the balloon is inflated. Such a bond may be achieved using any well known technique, for example, adhesives or ultrasonic bonding. Because of the typically high inflation pressures employed for inflation of the balloon, there is a wide range of choice of temporary bonding techniques. In other embodiments of the invention, the balloon may be maintained in a wrapped position by a deformable stint or generally tube-shaped material. Once the balloon is introduced into the region of stenosis and inflated, the deformable stint can remain in place, maintaining the artery lumen open.

FIGS. 5E-5F illustrate a device similar to the one depicted in FIGS. 5C-5D. However, the guidewire contained within this device is lower in profile relative to the guidewire contained within the device depicted in FIGS. 5C-5D. Again wrapping and reversible bonding of the balloon are used to confer column strength. FIG. 5E illustrates the configuration of the device during inflation and FIG. 5F illustrates the wrapped deflated configuration of the same device. Reducing the profile of the guidewire permits the construction of a dilatation system with a particularly low balloon profile. Wrapping the "balloon-like" component around the guidewire also fixes the coaxial relationship of the catheter and the wire. In this embodiment of the invention, the balloon is wrapped in such a manner that the folds 54 permit rotational movement of the wire contained therein, and yet limit the corresponding coaxial movement. This configuration permits use of the guidewire for column strength for the entire catheter system. In effect, the force required to advance the catheter within the confines of a patient's vasculature can be applied to the guidewire and not the catheter component. This permits the construction of the shaft of the device with thinner walls relative to other catheters. Thus, this configuration permits the construction of a vented single channel thin walled ultra-low profile smooth, flexible, vented dilatation balloon catheter that provides superior torque delivery, pushability, trackability, hydraulic performance, and guidewire compatibility relative to prior art catheters that permit complete withdrawal of the catheter from the guidewire. To facilitate withdrawal, transition zones connecting the low profile segment of the wire to the balance of the guidewire are tapered as shown in FIG. 5F.

FIGS. 6A-6E illustrate the use of a segment of polyimide tubing, or other suitable material, to provide column strength for the balloon components of catheters that can be withdrawn over guidewires and yet not accept the intra-operative introduction of an exchange wire therethrough. The clear zone (appearing white in the drawings) within each guidewire indicates the region of the wire rendered smooth and, therefore, the location of the fluid-tight seal. FIG. 6A is a reference diagram that illustrates the segment of the catheter contained in each of the subsequent diagrams.

FIGS. 6B and 6F illustrate the tubing 71 extending from the proximal portion of the balloon to the distal portion with a seal being formed at the distal portion. This tubing is free to rotate about the guidewire. Thus, the guidewire can rotate easier than absent the tubing. The tubing also provides column strength and prevents the balloon from collapsing on the guidewire. The tubing 71 is maintained in position proximally by a protrusion 65 extending inward from the catheter wall and distally by tubing 78 that is bonded to the balloon. FIG. 6C illustrates a similar catheter wherein the tubing 71 is bonded to the interior of the distal portion of the balloon. In this case the seal is formed at the opposite end of the balloon and the stint does not rotate.

FIGS. 6D and 6G illustrates a structure similar to FIG. 6B; however, the tubing is bonded to a single protrusion 65, or bonded to the luminal surface of the catheter. In FIG. 6E, the tubing 71 is bonded both to the distal end of the balloon and the catheter wall. The proximal bond is eccentric and permits the passage of fluid.

FIG. 7A-7H illustrate a series of single channel, vented "semi-movable" dilatation catheter systems. The features that distinguish these devices from the previous ones are: (1) the profile of the guidewires contained within the confines of the catheter components of these systems, (2) the permanence of the guidewires within these catheters, and (3) the smooth transition zone between the guidewire and the catheter components of these systems. Each guidewire contains a very low profile segment that extends the length of the catheter. This guidewire configuration permits the construction of lower profile catheter systems relative to the previously described catheters.

The guidewires contained within these devices cannot be removed. In essence, these wires are so low in profile and so delicate that they cannot tolerate the abuse that stand alone conventional profile guidewires receive during a routine angioplasty procedure. Thus, the catheter shafts of these devices function to protect these delicate wires. These wires, however, can be fully rotated and advanced in a limited coaxial direction. The use of these systems clearly obligates sacrificing intraluminal access during the process of a catheter exchange.

Each device depicted in FIG. 7 further contains a streamlined transition zone 88 (see FIG. 7B) between the tip of the guidewire 84 and the distal end of the balloon component 55. This feature significantly contributes to the ease with which these devices can be advanced within the confines of a stenosis.

Although there exist prior art "semi-movable" dilatation balloon/catheter systems, these devices contain dual lumen catheter shafts with distinct guidewire channels that extend the length of these devices. Hence these prior art devices have larger profiles and inferior hydraulic performance characteristics compared to the systems described herein. In addition, the hydraulic channels of such prior art catheters frequently do not contain air vents.

FIG. 7A is a reference diagram that contains an inset which is expanded in FIGS. 7C-7G to more clearly depict the corresponding region of the catheter.

FIG. 7B is an enlarged view of the transition zone 88 between the tip of the guidewire and the leading edge 55 of the catheter component of each of the systems illustrated in FIGS. 7A-7H. The distal aspect of the catheter, which is composed of a segment of polyimide tubing 71 bonded to the luminal surface of the catheter tip 55, can be constructed with outside dimensions that approximate the corresponding dimensions of the guidewire tip.

FIG. 7C is a reference diagram that illustrates the coaxial mobility of the guidewire. In general, for a conventional length angioplasty catheter, the guidewires of these systems can be advanced a distance 89 of approximately 30 cms. relative to the corresponding catheter components.

FIG. 7D is an enlarged view of the distal aspect of the device depicted in FIGS. 7A-7C. This device does not contain a central tubular component within the balloon. The balloon requires wrapping and reversible adhesives or other temporary bonding means for column strength. This configuration provides a particularly low profile single channel vented, high performance, flexible, highly steerable and trackable dilatation balloon catheter/guidewire system, with a low coefficient of friction and smooth guidewire/catheter transition zone that contains a permanently installed semi-movable guidewire. The catheter has a streamlined transition zone between the guidewire and the catheter.

FIGS. 7E-7F illustrate similar devices that contain polyimide or other type tubular stints 71 within the balloon to provide column strength for the balloon 52. These stints 71 circumvent the need for reversible adhesives in the construction of these devices. In the most simple embodiment, these polyimide tubular elements are glued to a region of the luminal surface of the shaft tubing 66.

FIG. 7G-7H illustrate the use of a removable central tubular element in the construction of a low profile high performance "semi-movable" dilatation device. This device is similar in many respects to the device depicted in FIGS. 5A and 5B. The difference is that the profile of the guidewire and hence the profile of the composite device, is smaller.

FIGS. 8A-8H illustrate the distal aspect 50 of a series of low profile, single channel, vented, high performance fixed-wire devices that contain infinitely rotatable guidewires disposed therein. There exist prior art "fixed-wire" devices. However, the construction of these prior art devices requires bonding the distal aspect of the "balloon-like" component onto a region near the distal aspect of the guidewire contained therein. As previously indicated, the creation of a bond between these two components results in several functional limitations.

The use of a seal of our invention at the junction of the balloon and guidewire in conjunction with a means for providing column support for the balloon that does not limit the rotational mobility of the guidewire relative to the catheter component of the system permits the construction of single channel, vented, "fixed-wire" dilatation systems of equally low profile, that do not contain bonds between the catheter and guidewire components. This permits the construction of "fixed-wire" systems with enhanced torque delivery, infinite guidewire rotatability, superior steerability, and diminished propensity to sustain tip fracture relative to the prior art. The use of our seal further circumvents the need to include torque-limiters in the construction of these devices.

FIG. 8A is a reference diagram that contains an inset which is expanded in FIGS. 8B-8F to illustrate a corresponding region of the catheter.

FIG. 8B is a profile view of the distal aspect 50 of the device pictured in FIG. 8A. This device does not contain a central tubular component within the balloon. The balloon requires wrapping and reversible adhesives for column strength. This configuration provides a low profile, single channel high performance, hydraulically competent vented "fixed-wire" dilatation balloon catheter/guidewire system with a fully-rotatable guidewire, that has a streamlined transition zone between the guidewire and the catheter component of the system.

FIGS. 8C-8D illustrate similar "fixed-wire" devices that contain polyimide tubular stints 71 within the confines of the respective balloons. In FIG. 8C the stint is divided into two portions, one of which 71 is not bonded to the balloon, while the other portion 79 is bonded to the balloon. This configuration permits independent coaxial rotation of tubing 71 relative to both the catheter and guidewire components of the system and enables the guidewire to rotate more easily within the confines of the balloon relative to systems that employ non-rotating stints. In FIG. 8D the stint 71 is in one piece. It extends through the balloon, and it is bonded to the distal luminal surface of the balloon bonded to the balloon. These stints provide column strength for the respective balloons 52 and circumvent the need to employ reversible adhesives in the construction of these devices. Again, the interface between the guidewire and the distal central tubular element functions as a vent for the hydraulic channel. Of course, stint 71 can be bonded to the distal end of the balloon or eccentrically bonded to the shaft of the catheter (not shown) or both.

FIG. 8E illustrates a "fixed-wire" system that employs a stint that has been bonded to the guidewire. This stint again affords column strength to the balloon without compromising the rotational mobility of the balloon relative to the guidewire. Depending upon the application, this stint 96 need not be bonded to the wire. Instead, it can be tightly fitted thereon. The stint may comprise polyimide, or in some embodiments, a relatively opaque material (e.g., gold or platinum, etc.), thereby providing a marker for the location of the balloon (e.g., a marker chip).

FIG. 8F illustrates a "fixed-wire" system that is similar, in many respects, to the system depicted in FIG. 8E. However, the stint has been rendered shorter. Again, the stint 96 affords column support for the balloon and a radio-opaque material can be used in the manufacture of this stint 96. This approach permits the manufacture of a device that contains a lower profile and more flexible deflated balloon component relative to the device depicted in FIG. 8F. In this case, the stint does not contribute to the rigidity or profile of the balloon component of the system. In short, this configuration permits the manufacture of a low profile, infinitely rotatable, vented, highly "steerable," "fixed-wire" device that contains a balloon marker and that is not prone to guidewire fracture or wrap-mediated balloon rupture and that does not require a "torque limiter."

FIGS. 8G-8I illustrate other "fixed-wire" devices that rely upon the use of a marker chip 84 on the guidewire and a central tubular stint 71 to provide column strength for the balloon component of the device. In the case of the devices depicted in FIGS. 8G and 8H, the seals are at opposite ends of the balloon components of these devices.

FIGS. 9A-9G are side views of a variety of configurations for the proximal segments of the devices illustrated in FIGS. 3-8.

FIGS. 9A and 9A' are a side view and cross-section of a proximal segment 30 of a prior art coaxial dilatation balloon catheter that has been coupled, by a luer-lock fitting 36/136, to a prior art Y-adapter 130. The Y-adapter contains an O-ring 139 disposed between two independently movable structures 131/133, that functions to prevent blood loss from the guidewire channel 42. Clockwise rotation of the proximal component of the device 131 results in the compression of the O-ring 139, which in turn creates a seal between the adapter and the guidewire 80. The Y-adapter derives its name from the perfusion port 134 that connects at an oblique angle.

Although these devices permit coaxial movement of the guidewires contained therein, without significant blood loss, there are significant functional limitations to the use of these devices. For example, the O-ring valve 139 usually requires constant adjustment throughout the course of a standard angioplasty procedure. This constitutes a significant distraction for the operator. Loosening the O-ring permits movement of the guidewire. However, this procedure renders the valve incompetent and precludes satisfactory assessment of the pressure contained within the guidewire channel 42. Commonly, the pressure contained in this channel is monitored to provide some assessment concerning the patient's hemodynamic status. Opening the O-ring thus precludes conventional assessment of the patient's systemic blood pressure. Tightening the O-ring permits inspection of the patient's hemodynamics. However, this procedure commonly seizes the guidewire within the Y-adapter and precludes manipulation of this component of the system. For these reasons, the use of a conventional Y-adapter frequently requires intermittent tightening and loosing of the O-ring valve to permit intermittent wire movement and hemodynamic reassessment.

There are several additional disadvantages to the use of conventional Y-adapters, including the fact that these devices are prone to collect blood clots within the chamber 138 immediately adjacent the O-ring. Unlike the other channels within this device, chamber 138 cannot be flushed with fluid introduced into the device via the flush port 134. Hence this channel tends to collect blood clots when guidewires are withdrawn. Thus, the use of these devices predisposes the patient to an increased risk of embolic complications.

FIG. 9B illustrates the proximal aspect 30 of a dual channel catheter that contains a seal of our invention between the luminal surface of the catheter 71 and the outside surface of the guidewire 80. This seal provides several advantages relative to the prior art. It eliminates the need for a conventional Y-adapter, yet provides a seal that permits simultaneous guidewire movement and hemodynamic reassessment. It prevents the collection of embolic material. Because it requires no adjustment, it does not represent a source of distraction.

FIG. 9C illustrates the use of the aforementioned seal in the construction of a Y-adapter. The central lumen 138 of this device is configured such that it does not contain a blind lumen that can collect embolic material.

FIGS. 9D–9E illustrate the design of the proximal aspects 50 of devices that contain movably disposed central tubular elements 44. (See FIGS. 5A, 5B, 7G and 7H.) This design permits withdrawal of the central element beyond the level of the flush channel 134. The seal between the catheter shaft 48 and the guidewire 80 consists of two coaxial interfaces as shown best in FIG. 9E. The first interface is disposed between the two tubular elements that comprise the catheter shaft 44,48 and the second is disposed between the central tubular shaft 44 and the guidewire 80.

FIGS. 9F–9G illustrate the construction of the proximal aspect 50 of single channel devices using our invention. FIG. 9F illustrates a device constructed with a luer-lock fitting 36 at the distal end, which can be coupled to a conventional or modified Y-adapter. FIG. 9G illustrates a seal 1 of our invention used in the construction of the proximal end 30 of these devices.

FIGS. 10A–10E illustrate a series of guidewire configurations that can be used in conjunction with the devices described herein. The wires illustrated in FIGS. 10A–10C are intended for use in conjunction with "over the wire" systems. The wire illustrated in FIGS. 10D and 10E are intended for use in "semi-movable" and "fixed-wire" systems. FIG. 10E is an enlarged phantom view of the wire contained within the inset of FIG. 10D. FIGS. 10F–10P illustrate several "balloon-on-a-wire" systems.

FIGS. 10A–10C illustrate guidewires that contain segments with a smooth surface. FIG. 10A illustrates a segment of polyimide tubing 71 bonded to the surface of a guidewire of conventional design to provide a region with a smooth surface. In FIG. 10A the guidewire has a progressively tapering core 155 with a coiled outer layer 152 bonded to the core by suitable means 170.

FIG. 10B illustrates polyimide tubing 71 installed over a region of the wire coil of relatively reduced profile 166 to permit the construction of a guidewire of uniform surface dimensions that contains a smooth segment. FIG. 10C illustrates polyimide tubing 71 installed over a flexible/elastic material 158 in the construction of a guidewire of uniform dimensions that contains a smooth segment. The feature that distinguishes the latter wire from the previous two wires is the composite rigidity of the smooth segment. The smooth segments of the wires illustrated in FIGS. 10A and 10B are more rigid than the corresponding segment of the wire illustrated in FIG. 10C. Polyimide is a relatively rigid material and hence, the direct bonding of a segment of polyimide tubing to a guidewire enhances the rigidity of the composite structure. The embodiments depicted in FIGS. 10A and 10B are particularly applicable to circumstances where enhanced rigidity is desirable. The extent to which the polyimide affects the rigidity of the composite segment can be modified by changing the wall thickness of the polyimide used in the creation of the inner member of the interface; however, this approach does not permit the construction of a composite segment with flexibility commensurate with the adjacent components of the wire. Alternatively, the polyimide can be applied over an elastic material 158 to diminish the rigidity of the composite structure. (See FIG. 10C.) This approach provides the smooth component of the guidewire with enhanced flexibility relative to the previous embodiments. With the proper combination of materials, this configuration permits the construction of a guidewire with relatively uniform flexibility throughout its length that contains a segment with a smooth surface. Although these Figures depict various methods which can be used to construct segments of wires with smooth surfaces, it should be understood that this review is not intended to be exhaustive and that our seal will function with any guidewire of any configuration that provides a surface that conforms to the luminal surface of the sleeve component of the catheter.

FIG. 10D is an off-center view of the distal aspect of the guidewire contained within the "semi-movable" and "fixed-wire" devices that employ our seal. FIG. 10E is an enlarged profile view of the guidewire component contained within the inset of FIG. 10D. This wire contains a mandril 150 that is continuous with a progressively tapered core element 155. A flexible wire coil 152 is attached to the core element by a solder joint 174 and a thin wire ribbon 162. This configuration permits the construction of a guidewire that contains segments of progressively increasing flexibility. In one embodiment, the proximal aspect of the wire coil 84 is tapered outward to accommodate the tip of the catheter movably disposed on the core element 155. The insertion of the catheter tip 55 within the confines of the guidewire coils enhances the structural integrity of this relatively delicate region of the catheter and provides a smooth transition zone between the guidewire component and the catheter component of the system. In the preferred embodiment, the junction of the guidewire and catheter permits full rotational and coaxial movement. The insertion of a rotationally disposed catheter tip within the confines of the guidewire coil constitutes a significant departure from convention.

FIGS. 10F–10I illustrate "balloon-on-a-wire" systems of our design, which, as the name implies, refers to guidewires 150 containing lumens 190 that communicate with balloons disposed along the length of the wires. Although prior art "balloon-on-a-wire" systems exist, these systems contain balloons that are bonded immovably to the guidewires. Such prior art configurations compromise the transmission of torque along the length of the device and predispose the device to the development of fractures within the core elements.

As shown in FIGS. 10F and 10H, the "balloon-on-a-wire" system of our invention consists of a guidewire that extends the length of the system, together with a balloon component 174, that is rotatably disposed thereon. The guidewire consists of several components that are bonded together to form a single unit. These components include a hub 148, shaft 150, core element 157, flexible coil 181, and coil tip 164. The shaft 150 of the device is composed of stainless steel hypo-tubing. It is welded to the core element in region 152. A solder joint is used to join the core element 157 to the flexible coil 181.

The balloon component 174 consists of a balloon 52 and two segments of polyimide tubing 71, 170 that are bonded together at location 172 to form a single unit. (See FIG. 10H.) Polyimide is used in the construction of the distal catheter shaft 170 because it is more resilient than stainless steel. It will accept bending more readily, without sustaining kinks relative to stainless steel. Hence, it is more suitable for use in the construction of this component of the shaft, which frequently must be introduced within the confines of tortuous blood vessels. The proximal and distal aspects of this balloon unit 174 employ seals 1 of our invention with the corresponding elements of the guidewire component of the system. The use of these seals in the construction of this device permits the infinite independent rotational motion of the balloon component 174 relative to the guidewire component, with preserved hydraulic competence. This rotational mobility of the guidewire relative to the balloon component precludes the need to rotate the balloon in conjunction with the guidewire during manipulation of the device within the confines of the vasculature. This feature, in turn, enhances the transmission of torque along the length of the core element, enhances the steerability of the device, and diminishes the propensity for the balloon to wrap with the application of torque. Most significantly, it diminishes the propensity of the device to sustain tip fracture.

The configuration of the guidewire component limits the coaxial mobility of the balloon component. The insertion of the tip of the balloon 55 within the confines of the guidewire coil 88 provides additional structural support within the transition zone between the balloon and guidewire, the region most prone to sustain fractures in the prior art. Because polyimide tends to expand during sterilization, the seal 1 in region 176 can be constructed in such a manner that it will accept expansion, e.g., an expansion joint.

FIG. 10F illustrates one embodiment of our "balloon-on-a-wire" device in which all of the components are coaxial in disposition. Alternatively, our device can be constructed with components that are not coaxial, as illustrated in FIG. 10G. In the case of this latter design, the guidewire component is constructed by bonding the core element 157 directly onto the lumenal surface of the hypo-tubing 150 that comprises the shaft of the device. Similarly, the balloon component is constructed by bonding the outer surface of member 71 directly onto the luminal surface of the polyimide tubing 170. Given the length-to-width ratio of "balloon-on-a-wire" devices, the use of off-center bonds does not compromise the functional characteristics of the device and simplifies the process of catheter construction.

FIG. 10I illustrates an alternative embodiment of the device depicted in FIG. 10H. In this device, a marker chip 183, typically gold, provides a marker for the balloon and combined with tube 71 provides column strength for the balloon component of the catheter.

FIGS. 11A–11E are schematic representations of complete balloon angioplasty systems. FIG. 11A, typical of the prior art and described further below, includes a guiding catheter, dilatation balloon catheter, guidewire and supportive apparatus. FIGS. 11B–11E are similar representations of a substantially lower profile composite system of our invention that contains multiple seals 1 which are disposed between a variety of independently movable surfaces. The use of our seal permits the construction of a variety of dilatation systems containing multi-purpose hydraulic channels. The system illustrated in FIGS. 11B–11E illustrates several advantages inherent to the use of these seals in the construction of composite catheter systems. FIGS. 11B–11E illustrate that seals of our invention have particular application to the construction of composite catheter systems containing a wide variety of devices, such as dilatation balloon/laser systems, dilatation balloon/atherectomy systems, dilatation balloon/intravascular ultrasound systems, independent atherectomy systems, etc., that require the transmission of hydraulic pressure or the conveyance of fluid within the confines of the device.

FIG. 11A is a profile view of a complete prior art catheter system used to perform an angioplasty. The dilatation balloon catheter, prepared with a guidewire 80 is introduced into the coronary vasculature via the lumen 240 of a guiding catheter 200. The lumen 240 of the guiding catheter is coupled to a three-way manifold 270 and a syringe 280 by a Y-adapter 130 and a perfusion channel 260. The guidewire lumen 42 of the dilatation catheter is coupled similarly via a Y-adapter 130' to a three-way manifold 270' and a corresponding injection syringe 284. The hydraulic channel 46 of the dilatation catheter is coupled directly to an inflation syringe 282. The composite structure contains three concentric tubes 44,48,200 and three independent lumens 42,44,240 at the level of introduction through the skin 300. (See the cross-sectional view, FIG. 11G.) The application of pressure to the syringe 280 results in the injection of contrast into the vasculature distal to the guiding catheter and permits the performance of an intraoperative angiogram. The application of pressure to syringe 282 results in the transmission of hydraulic pressure along the length of the dilatation catheter and inflation of the "balloon-like" component of this system. The application of pressure to syringe 284 results in the introduction of contrast via the guidewire channel 42 of the balloon catheter and permits the performance of selective angiography of the vessel containing the balloon catheter. The three-way manifolds 270, 270' communicate variously with pressure transducers, flush ports and contrast reservoirs and permit intra-operative assessment of the patient's hemodynamic status. This system is bulky and contains considerable duplication of effort.

FIG. 11E is a profile view of a vented ultra-low profile single-channel dilatation balloon catheter system of our invention. It contains a pre-wrapped/reversibly bonded dilatation balloon 52, a distal catheter shaft 66 of precise and uniform dimensions, a fenestrated proximal catheter shaft 110, and a non-uniform guidewire 80. FIGS. 11B–11D illustrate the use of the previous dilatation catheter system in conjunction with one embodiment of a very low profile guiding catheter of our invention.

FIG. 11B is a profile view of a guiding catheter 210 of our design that contains a polyimide sleeve 71 that precisely accommodates the outside dimensions of the aforementioned catheter shaft 66. The lumen of this guiding catheter communicates with a three-way adapter 270 and multi-purpose injection syringe 286.

FIG. 11C illustrates the appearance of the overall system following introduction of the dilatation catheter system. Note that the shaft of the dilatation catheter forms a seal with the two polyimide sleeves disposed within the proximal and mid-portions of the guiding catheter lumen, and that the presence of the fenestration within the dilatation catheter shaft 110 permit direct communication between the multi-purpose perfusion channel 266 and the multipurpose hydraulic channel 64 of the dilatation catheter.

FIGS. 11B–11D illustrate that this system can be used to perform coronary arteriography (FIG. 11B); perform selective coronary arteriography (FIG. 11C); and transmit hydraulic pressure (FIG. 11D) depending upon the presence or absence of the dilatation system within the channel of the guiding catheter and depending upon the location of the guidewire relative to the dilatation system. This system permits the performance of all three of these functions with a particularly low-profile device. Note that this system entails substantially less duplication of effort relative to convention. Additionally, the hydraulic pressure is conducted largely by the lumen of the guiding catheter, in the case of this system. Given the relationship between hydraulic performance and hydraulic channel dimensions, this system permits the construction of a high performance, ultra-low profile angioplasty system.

Although numerous embodiments of the invention have been described and discussed above, it will be apparent to those of skill in the art that by employing our invention, variations may be made in these embodiments to achieve other catheter designs having beneficial features. The scope of our invention may be determined from the following claims.

We claim:
1. A seal for a catheter comprising:
   a first region of selected material disposed on a first portion of the catheter, the first region having a first surface contour;
   a second region of desired material disposed on a second portion of the catheter, the second region having a second surface contour corresponding to the first surface contour, the second region being movable with respect to the first region;
   said first and second regions being positioned such that said first and second contours are facing each other to define a facing portion, wherein said facing portion separates first and second volumes and wherein at least one of said first and second volumes containing a liquid; and
   wherein the first region and the second region are spaced apart by a distance sufficiently small to prevent said liquid from flowing therebetween.
2. A seal as in claim 1 wherein the second portion is movable with respect to the first portion.
3. A seal as in claim 1 wherein the second portion of the catheter is movable in a first direction with respect to the first portion of the catheter.
4. A seal as in claim 3 wherein the first direction is linear.
5. A seal as in claim 3 wherein the first direction is rotation.
6. A seal as in claim 1 wherein the first surface comprises an annulus.
7. A seal as in claim 6 wherein the second surface comprises an annulus.
8. A seal as in claim 1 further comprising a lubricant introduced between the first region and the second region.
9. A seal as in claim 8 wherein the lubricant prevents a gas from flowing between the first region and the second region.
10. A seal as in claim 1 wherein the selected material comprises stainless steel.
11. A seal as in claim 10 wherein the desired material comprises polyimide.
12. A seal as in claim 1 wherein the first region comprises a rod.
13. A seal as in claim 12 wherein the second region comprises an annulus.
14. A seal as in claim 1 wherein the first region is disposed on a guidewire.
15. A seal as in claim 14 wherein the second region is disposed on a wall of the catheter.
16. A seal as in claim 15 wherein the selected material comprises stainless steel and the desired material comprises polyimide.

* * * * *

REEXAMINATION CERTIFICATE (3490th)
United States Patent [19]
Kraus et al.

[11] B1 5,209,728
[45] Certificate Issued Apr. 14, 1998

[54] LOW PROFILE, HIGH PERFORMANCE INTERVENTIONAL CATHETERS

[75] Inventors: Jeff Kraus, San Jose; Robert D. Lashinski, Cupertino, both of Calif.

[73] Assignee: Danforth Biomedical, Inc., Menlo Park, Calif.

Reexamination Request:
No. 90/003,907, Jul. 31, 1995

Reexamination Certificate for:
Patent No.: 5,209,728
Issued: May 11, 1993
Appl. No.: 946,828
Filed: Sep. 16, 1992

Related U.S. Application Data

[63] Continuation of Ser. No. 430,702, Nov. 2, 1989, abandoned.
[51] Int. Cl.[6] .................... A61M 29/00; A61M 25/10
[52] U.S. Cl. ............................................ 604/96; 604/280

[56] References Cited

U.S. PATENT DOCUMENTS

| | | | |
|---|---|---|---|
| 4,976,720 | 12/1990 | Machold et al. | 606/194 |
| 5,032,113 | 7/1991 | Burns | 604/96 |
| 5,047,045 | 9/1991 | Arney et al. | 606/194 |
| 5,135,494 | 8/1992 | Engelson et al. | 604/99 |

*Primary Examiner*—Michael H. Thaler

[57] ABSTRACT

A catheter, having a substantially fluid-tight seal is provided. The seal can be used in a number of catheters, including an angioplasty catheter. The seal includes surfaces that are independently movable relative to one another. The effectiveness of the seal depends on the proximity of the surfaces, the surface are at the interface, pressure differential and viscosity of the fluid. The seal is used in connection with providing fluid-tight channels with surfaces that are relatively movable and to circumvent the need to separate hydraulic channels from other channels so that catheters can be provided with fewer channels. Further, catheters and catheter systems with smaller shaft dimensions or larger hydraulic channel dimensions is made possible. Balloon catheters using this seal have enhanced torque delivery and directional control.

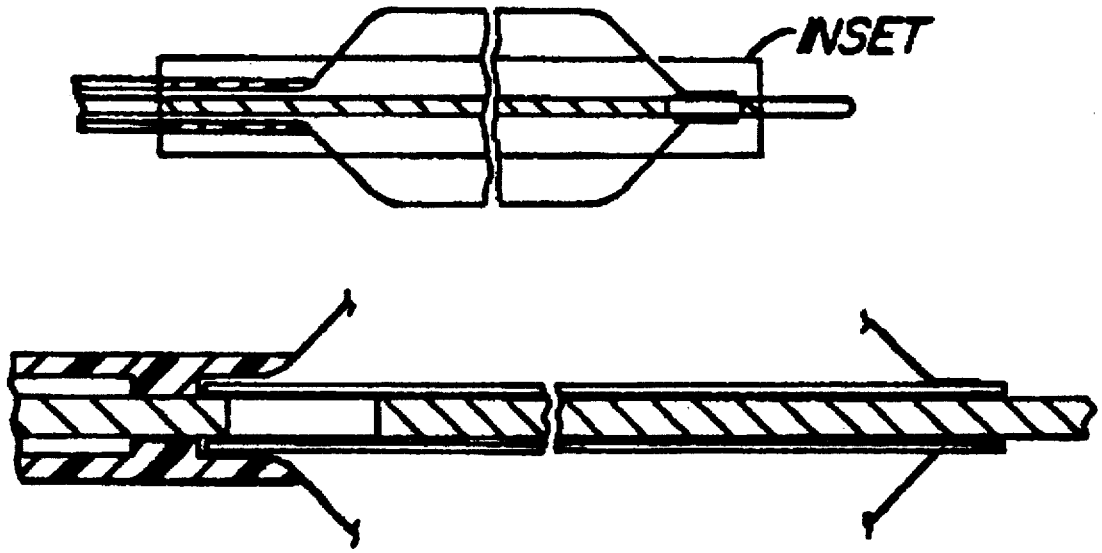

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–16 having been finally determined to be unpatentable, are cancelled.

New claims 17–21 are added and determined to be patentable.

*17. A catheter having a balloon at a distal end thereof, the balloon having an interior that is inflatable upon pressurization with inflation media and a seal preventing leakage of inflation media from the catheter, the seal comprising:*

*a first region disposed on a first portion of the catheter and having a first surface contour; and*

*a second region disposed on a second portion of the catheter, the second region being movable with respect to the first region and having a second surface contour corresponding to the first surface contour, the second region being movable with respect to the first region, the first and second regions spaced apart by a distance sufficiently small to prevent inflation media from flowing therebetween, thereby forming a seal, the seal positioned to commence substantially at the proximal end of the balloon and to extend distally into the balloon, and to separate a first volume within the catheter that is in communication with the balloon interior from a second volume that is in communication with the exterior of said catheter.*

*18. A seal as in claim 17 further comprising a lubricant introduced between the first region and the second region.*

*19. A seal as in claim 17 wherein the lubricant prevents a gas from flowing between the first region and the second region.*

*20. A seal as in claim 17 wherein the first region is disposed on a guidewire.*

*21. A seal as in claim 17 wherein the first region is disposed on a guidewire and the second region is disposed on a wall of the catheter.*

* * * * *